US012311020B2

(12) United States Patent
Moser et al.

(10) Patent No.: US 12,311,020 B2
(45) Date of Patent: *May 27, 2025

(54) IMMUNOGENIC COMPOSITIONS AGAINST INFLUENZA

(71) Applicant: FluGen, Inc., Madison, WI (US)

(72) Inventors: Michael J. Moser, Madison, WI (US); Yasuko Hatta, Madison, WI (US); Pamuk Bilsel, Madison, WI (US)

(73) Assignee: FluGen, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/747,713

(22) Filed: May 18, 2022

(65) Prior Publication Data
US 2023/0099147 A1  Mar. 30, 2023

Related U.S. Application Data

(63) Continuation of application No. 16/488,906, filed as application No. PCT/US2018/019653 on Feb. 26, 2018, now Pat. No. 11,344,616.

(60) Provisional application No. 62/464,019, filed on Feb. 27, 2017.

(51) Int. Cl.
A61K 39/145 (2006.01)
A61K 39/295 (2006.01)
C12N 7/00 (2006.01)

(52) U.S. Cl.
CPC .......... A61K 39/145 (2013.01); A61K 39/295 (2013.01); C12N 7/00 (2013.01); C12N 2760/16134 (2013.01); C12N 2760/16171 (2013.01); C12N 2760/16234 (2013.01); C12N 2760/16271 (2013.01)

(58) Field of Classification Search
None
See application file for complete search history.

(56) References Cited

U.S. PATENT DOCUMENTS

| 2014/0127249 A1 | 5/2014 | Bilsel et al. |
| 2016/0228534 A1 | 8/2016 | Bilsel et al. |
| 2017/0106077 A1 | 4/2017 | Lefebvre et al. |

FOREIGN PATENT DOCUMENTS

| CN | 103781901 A | 5/2014 |
| JP | 2011-506264 A | 3/2011 |
| JP | 2012-525370 A | 10/2012 |
| JP | 2013-504556 A | 2/2013 |
| JP | 2014-526883 A | 10/2014 |

(Continued)

OTHER PUBLICATIONS

Database GenBank [online], Accessin No. AF100376,<https://www.ncbi.nlm.nih.gov/nuccore/AF100376.1>, May 9, 1999 uploaded, [retrieved on Nov. 11, 2022], Definition: Influenza B virus B/Victoria/2/87 segment 7 M1 matrix protein (M) and BM2 protein (BM2) genes, complete cds.

(Continued)

Primary Examiner — M Franco G Salvoza
(74) Attorney, Agent, or Firm — Foley & Lardner LLP

(57) ABSTRACT

Disclosed herein are compositions and methods related to mutant viruses, and in particular, mutant influenza viruses. The mutant viruses disclosed herein include mutant M2 sequences, mutant BM2 sequences, and are useful in immunogenic compositions, e.g., as a quadrivalent vaccines. Also disclosed herein are methods, compositions and cells for propagating the viral mutants, and methods, devices and compositions related to vaccination.

8 Claims, 16 Drawing Sheets
Specification includes a Sequence Listing.

(56) References Cited

FOREIGN PATENT DOCUMENTS

| | | |
|---|---|---|
| JP | 7336990 B2 | 8/2023 |
| WO | WO-2008/068631 | 6/2008 |
| WO | WO-2010/125461 | 11/2010 |
| WO | WO-2011/030218 | 3/2011 |
| WO | WO-2012/177924 A2 | 12/2012 |
| WO | WO-2015/142671 A2 | 9/2015 |
| WO | WO-2015/195218 A1 | 12/2015 |
| WO | WO-2017/123976 A1 | 7/2017 |
| WO | WO-2018/073340 A1 | 4/2018 |
| WO | WO-2018/157028 A1 | 8/2018 |

OTHER PUBLICATIONS

Database GenBank [online], Accessin No. AF100378,<https://www.ncbi.nlm.nih.gov/nuccore/AF100378.1>, May 9, 1999 uploaded, [retrieved on Nov. 11, 2022], Definition: Influenza B virus B/Yamagata/16/88 segment 7 M1 matrix protein (M) and BM2 protein (BM2) genes, complete cds.

Goka et al. "Influenza A viruses dual and multiple infections with other respiratory viruses and risk of hospitalization and mortality," Influenza and Other Respiratory Viruses, vol. 7, No. 6 (2013) (pp. 1079-1087).

International Search Report and Written Opinion in International Application PCT/US18/19653 mailed on Aug. 2, 2018 (27 pages).

Wentworth, et al., "The NIAID Influenza Genome Sequencing Project," Oct. 2013, Influenza Research Database—Influenza B virus (B/Victoria/228/2007—BM2 Matrix protein 2, M1 Matrix protein 1—CY156267, retrieved from the Internet Aug. 26, 2019: https://www.fludb.org/brc/fluSegmentDetails.spg?ncbiProteinId=AGX23976&decorator=influenza&context=1529522650204>; p. 1, 1st paragraph; p. 1, Table 3.

"Influenza B virus (B/Victroria/228/2007) matrix protein (M1) and BM2 protein (BM2) genes, complete cds" GeneBank; Accession No. CY1256267; Oct. 16, 2013.

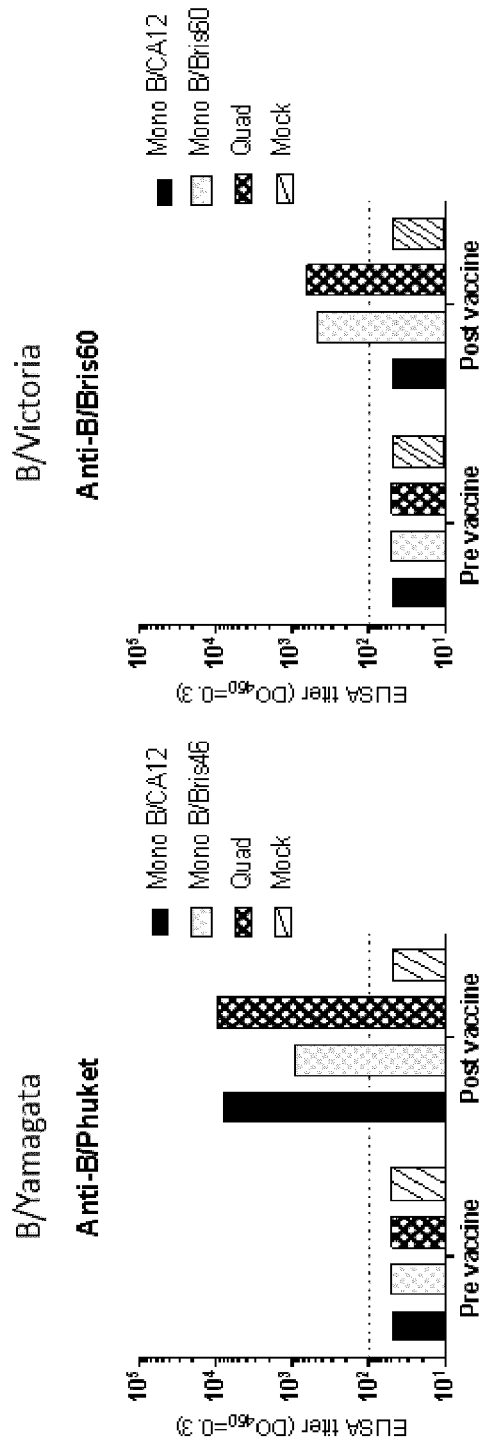

FIGURE 7A
FIGURE 7B
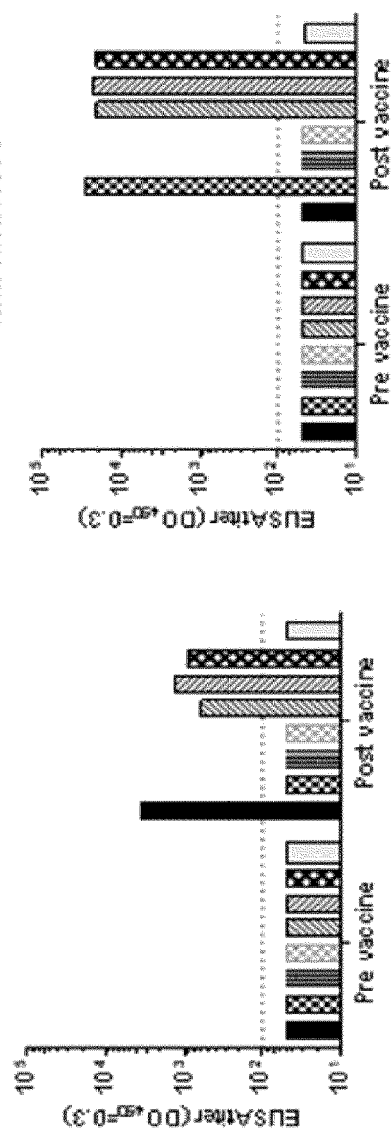
FIGURE 7C
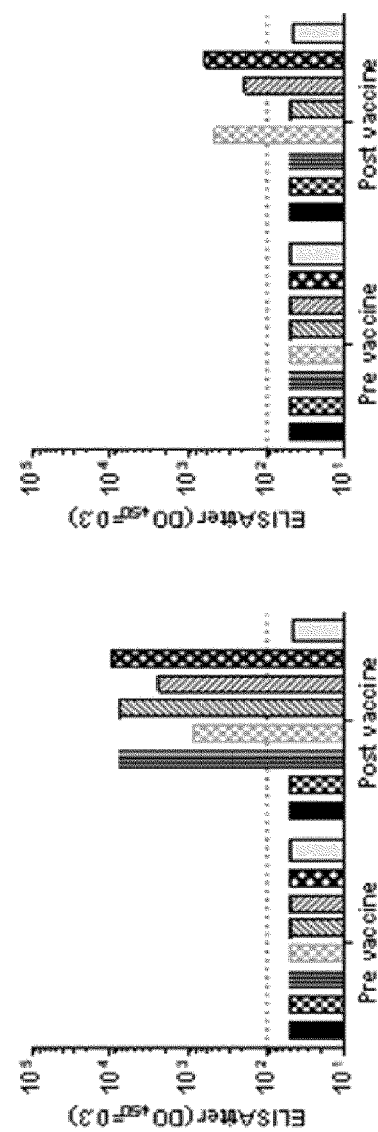
FIGURE 7D

IMMUNOGENIC COMPOSITIONS AGAINST INFLUENZA

CROSS-REFERENCE TO RELATED APPLICATION

The present application is a continuation of U.S. patent application Ser. No. 16/488,906, filed Aug. 26, 2019, now U.S. Pat. No. 11,344,616 issued May 31, 2022, which is a U.S. National Phase Application under 35 U.S.C. § 371 of International Application No. PCT/US2018/019653, filed Feb. 26, 2018, which claims the benefit of and priority to U.S. Application No. 62/464,019, filed Feb. 27, 2017, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Mar. 27, 2018, is named 090248-0238_SL.txt and is 18,149 bytes in size.

BACKGROUND

Influenza is a leading cause of death among American adults. Each year, about 36,000 people die from influenza, and more than 200,000 people are hospitalized. Influenza is a highly contagious disease that is spread by coughing, sneezing and through direct physical contact with objects that carry the virus such as doorknobs and telephones. Symptoms of influenza include fever, extreme fatigue, headache, chills and body aches; about 50 percent of infected people have no symptoms but are still contagious. Immunization is 50-60 percent effective in preventing influenza in healthy people under the age of 65, as long as the antigenicities of the circulating virus strain match those of the vaccine.

Vaccination is the main method for preventing influenza, and both live attenuated and inactivated (killed) virus vaccines are currently available. Live virus vaccines, typically administered intranasally, activate all phases of the immune system and can stimulate an immune response to multiple viral antigens. Thus, the use of live viruses overcomes the problem of destruction of viral antigens that may occur during preparation of inactivated viral vaccines. In addition, the immunity produced by live virus vaccines is generally more durable, more effective, and more cross-reactive than that induced by inactivated vaccines, and live virus vaccines are less costly to produce than inactivated virus vaccines. However, the mutations in attenuated virus are often ill-defined, and reversion is a concern.

SUMMARY

In one aspect, the present disclosure provides an immunogenic composition, wherein the composition is a multivalent composition comprising recombinant viruses from at least two influenza strains.

In some embodiments, the multivalent composition comprises: a) at least one engineered attenuated influenza A M2-deficient recombinant virus, wherein the engineered influenza A virus comprises a mutant M2 gene comprising SEQ ID NO: 1, SEQ ID NO: 2, or SEQ ID NO: 3; and b) at least one engineered attenuated influenza BM2-deficient recombinant virus, wherein the engineered influenza B virus comprises a mutant BM2 gene comprising SEQ ID NO: 6, SEQ ID NO: 7, SEQ ID NO: 8, SEQ ID NO: 9, SEQ ID NO: 10, or SEQ ID NO: 11. In some embodiments, the at least one influenza A virus is chosen from the group of H1N1 and H3N2 subtypes, and the at least one influenza B virus is chosen from the group of B/Yamagata and B/Victoria lineages.

In some embodiments, the multivalent composition comprises recombinant viruses selected from the group consisting of: a) two engineered attenuated influenza A M2-deficient viruses chosen from the group of H1N1 and H3N2 subtypes, wherein the A M2-deficient viruses comprise a mutant M2 gene comprising SEQ ID NO: 1, SEQ ID NO: 2, or SEQ ID NO: 3, and two engineered attenuated influenza BM2-deficient viruses chosen from the group of B/Yamagata and B/Victoria lineages, wherein the BM2-deficient viruses comprise a mutant BM2 gene comprising SEQ ID NO: 6, SEQ ID NO: 7, SEQ ID NO: 8, SEQ ID NO: 9, SEQ ID NO: 10, or SEQ ID NO:11; b) two engineered attenuated influenza A M2-deficient viruses chosen from the group of H1N1 and H3N2 subtypes, wherein the A M2-deficient viruses comprise a mutant M2 gene comprising SEQ ID NO: 1, SEQ ID NO: 2, or SEQ ID NO: 3, and one engineered attenuated influenza BM2-deficient virus chosen from the group of B/Yamagata and B/Victoria lineages, wherein the BM2-deficient virus comprises a mutant BM2 gene comprising SEQ ID NO: 6, SEQ ID NO: 7, SEQ ID NO: 8, SEQ ID NO: 9, SEQ ID NO: 10, or SEQ ID NO:11; c) one engineered attenuated influenza A M2-deficient virus chosen from the group of H1N1 and H3N2 subtypes, wherein the A M2-deficient virus comprises a mutant M2 gene comprising SEQ ID NO: 1, SEQ ID NO: 2, or SEQ ID NO: 3, and two engineered attenuated influenza BM2-deficient viruses chosen from the group of B/Yamagata and B/Victoria lineages, wherein the BM2-deficient viruses comprise a mutant BM2 gene comprising SEQ ID NO: 6, SEQ ID NO: 7, SEQ ID NO: 8, SEQ ID NO: 9, SEQ ID NO: 10, or SEQ ID NO:11; and d) one engineered attenuated influenza A M2-deficient virus chosen from the group of H1N1 and H3N2 subtypes, wherein the A M2-deficient virus comprises a mutant M2 gene comprising SEQ ID NO: 1, SEQ ID NO: 2, or SEQ ID NO: 3, and one engineered attenuated influenza BM2-deficient virus chosen from the group of B/Yamagata and B/Victoria lineages, wherein the BM2-deficient virus comprises a mutant BM2 gene comprising SEQ ID NO: 6, SEQ ID NO: 7, SEQ ID NO: 8, SEQ ID NO: 9, SEQ ID NO: 10, or SEQ ID NO:11.

In some embodiments, the multivalent composition is a quadrivalent composition comprising: a) two engineered attenuated influenza A viruses consisting of: i) H1N1 having a mutant M2 gene comprising SEQ ID NO: 1, and ii) H3N2 having a mutant M2 gene comprising SEQ ID NO: 1; and b) two engineered attenuated influenza B viruses consisting of: i) B/Victoria having a mutant BM2 gene comprising SEQ ID NO: 9 or SEQ ID NO: 11, and ii) B/Yamagata having a mutant BM2 gene comprising SEQ ID NO: 9 or SEQ ID NO: 11.

In some embodiments, the multivalent composition is a quadrivalent composition comprising: a) two engineered attenuated influenza A viruses consisting of: i) H1N1 having a mutant M2 gene comprising SEQ ID NO: 1, and ii) H3N2 having a mutant M2 gene comprising SEQ ID NO: 1; and b) one engineered attenuated influenza B viruses selected from the group consisting of: i) B/Victoria having a mutant BM2 gene comprising SEQ ID NO: 9 or SEQ ID NO: 11, and ii) B/Yamagata having a mutant BM2 gene comprising SEQ ID NO: 9 or SEQ ID NO: 11.

In some embodiments, the immunogenic compositions of the present disclosure further comprise a pharmaceutically acceptable carrier. In some embodiments, the immunogenic compositions of the present disclosure further comprise a pharmaceutically acceptable adjuvant. In some embodiments, the immunogenic compositions of the present technology are formulated for intranasal or intracutaneous administration.

In one aspect, the present disclosure provides a method of stimulating an immune response against influenza A and influenza B comprising administering to a subject in need thereof a multivalent immunogenic composition comprising: a) at least one engineered attenuated influenza A M2-deficient recombinant virus, wherein the engineered influenza A virus comprises a mutant M2 gene comprising SEQ ID NO: 1, SEQ ID NO: 2, or SEQ ID NO: 3; and b) at least one engineered attenuated influenza B M2-deficient recombinant virus, wherein the engineered influenza B virus comprises a mutant BM2 gene comprising SEQ ID NO: 6, SEQ ID NO: 7, SEQ ID NO: 8, SEQ ID NO: 9, SEQ ID NO: 10, or SEQ ID NO: 11.

In some embodiments, the at least one influenza A virus is chosen from the group of H1N1 and H3N2 subtypes, and the at least one influenza B virus is chosen from the group of B/Yamagata and B/Victoria lineages.

In some embodiments, the multivalent immunogenic composition comprises recombinant viruses selected from the group consisting of: a) two engineered attenuated influenza A M2-deficient viruses chosen from the group of H1N1 and H3N2 subtypes, wherein the A M2-deficient viruses comprise a mutant M2 gene comprising SEQ ID NO: 1, SEQ ID NO: 2, or SEQ ID NO: 3, and two engineered attenuated influenza BM2-deficient viruses chosen from the group of B/Yamagata and B/Victoria lineages, wherein the BM2-deficient viruses comprise a mutant BM2 gene comprising SEQ ID NO: 6, SEQ ID NO: 7, SEQ ID NO: 8, SEQ ID NO: 9, SEQ ID NO: 10, or SEQ ID NO:11; b) two engineered attenuated influenza A M2-deficient viruses chosen from the group of H1N1 and H3N2 subtypes, wherein the A M2-deficient viruses comprise a mutant M2 gene comprising SEQ ID NO: 1, SEQ ID NO: 2, or SEQ ID NO: 3, and one engineered attenuated influenza BM2-deficient virus chosen from the group of B/Yamagata and B/Victoria lineages, wherein the BM2-deficient virus comprises a mutant BM2 gene comprising SEQ ID NO: 6, SEQ ID NO: 7, SEQ ID NO: 8, SEQ ID NO: 9, SEQ ID NO: 10, or SEQ ID NO:11; c) one engineered attenuated influenza A M2-deficient virus chosen from the group of H1N1 and H3N2 subtypes, wherein the A M2-deficient virus comprises a mutant M2 gene comprising SEQ ID NO: 1, SEQ ID NO: 2, or SEQ ID NO: 3, and two engineered attenuated influenza BM2-deficient viruses chosen from the group of B/Yamagata and B/Victoria lineages, wherein the BM2-deficient viruses comprise a mutant BM2 gene comprising SEQ ID NO: 6, SEQ ID NO: 7, SEQ ID NO: 8, SEQ ID NO: 9, SEQ ID NO: 10, or SEQ ID NO:11; and d) one engineered attenuated influenza A M2-deficient virus chosen from the group of H1N1 and H3N2 subtypes, wherein the A M2-deficient virus comprises a mutant M2 gene comprising SEQ ID NO: 1, SEQ ID NO: 2, or SEQ ID NO: 3, and one engineered attenuated influenza BM2-deficient virus chosen from the group of B/Yamagata and B/Victoria lineages, wherein the BM2-deficient virus comprises a mutant BM2 gene comprising SEQ ID NO: 6, SEQ ID NO: 7, SEQ ID NO: 8, SEQ ID NO: 9, SEQ ID NO: 10, or SEQ ID NO:11.

In some embodiments, the multivalent immunogenic composition is a quadrivalent composition comprising: a) two engineered attenuated influenza A viruses consisting of: i) H1N1 having a mutant M2 gene comprising SEQ ID NO: 1, and ii) H3N2 having a mutant M2 gene comprising SEQ ID NO: 1; and b) two engineered attenuated influenza B viruses consisting of: i) B/Victoria having a mutant BM2 gene comprising SEQ ID NO: 9 or SEQ ID NO: 11, and ii) B/Yamagata having a mutant BM2 gene comprising SEQ ID NO: 9 or SEQ ID NO: 11.

In some embodiments, the multivalent immunogenic composition is a quadrivalent composition comprising: a) two engineered attenuated influenza A viruses consisting of: i) H1N1 having a mutant M2 gene comprising SEQ ID NO: 1, and ii) H3N2 having a mutant M2 gene comprising SEQ ID NO: 1; and b) one engineered attenuated influenza B viruses selected from the group consisting of: i) B/Victoria having a mutant BM2 gene comprising SEQ ID NO: 9 or SEQ ID NO: 11, and ii) B/Yamagata having a mutant BM2 gene comprising SEQ ID NO: 9 or SEQ ID NO: 11.

In some embodiments, the immunogenic compositions of the present disclosure further comprise a pharmaceutically acceptable carrier. In some embodiments, the immunogenic compositions of the present disclosure further comprise a pharmaceutically acceptable adjuvant. In some embodiments, the immunogenic compositions of the present disclosure are formulated for intranasal or intracutaneous administration.

BRIEF DESCRIPTION OF THE DRAWINGS

FIGS. 6A-6B are charts showing anti-HA IgG antibody titers elicited against influenza B virus post-inoculation with monovalent BM2SR and quadrivalent formulation. Representative BM2SR constructs: B/CA12 is B Yamagata BM2SR; B/Bris46 is B Victoria BM2SR. The quadrivalent formulation is a mix of the two BM2SR and H1N1 and H3N2 M2SR.

FIGS. 7A-7D are charts showing M2SR and BM2SR mutants elicit antibody responses against influenza A and influenza B viruses in multivalent formulations. Representative M2SR and BM2SR constructs: A/MA15 is H1N1 M2SR; A/HK4801 is H3N2 M2SR; B/CA12 is B Yamagata BM2SR-4; B/Bris46 is B Victoria BM2SR-4. The quadrivalent ("quad") formulation is a mix of all four. The trivalent ("tri") is a formulation of the indicated three viruses.

DETAILED DESCRIPTION

I. Definitions

Figure 1:
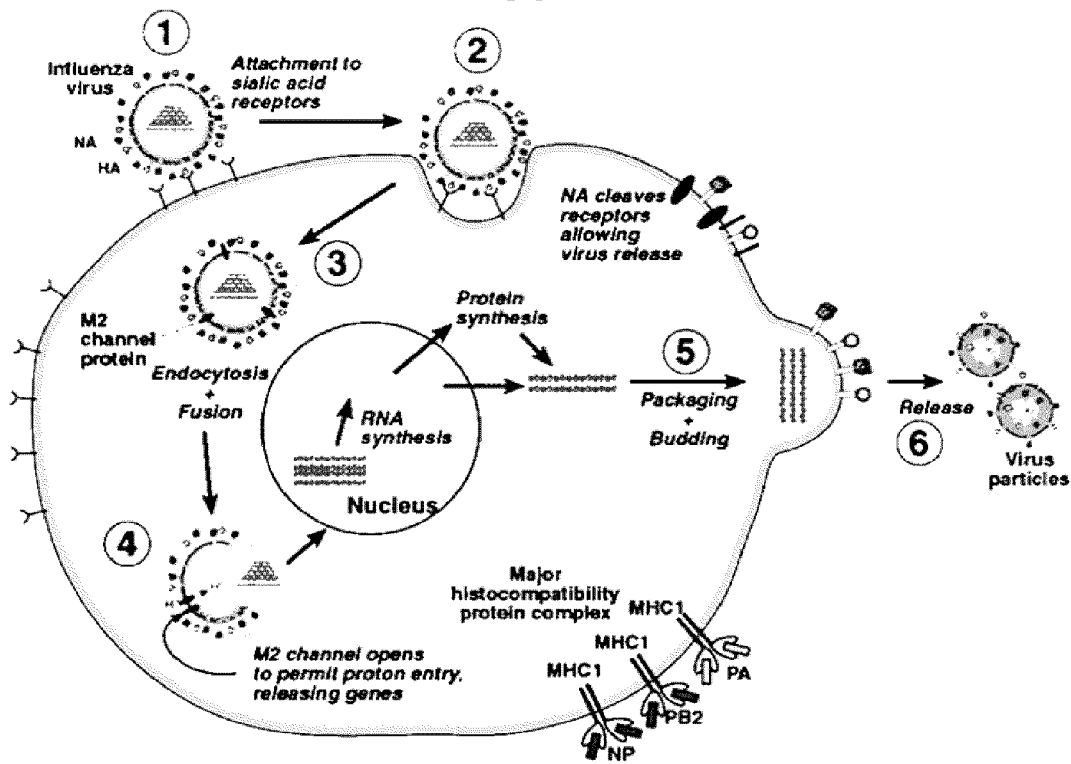
FIG. 1 is a graphic depicting the role of M2 ion channel in an influenza virus life cycle, wherein (1) the influenza virus attaches to sialic acid receptors on a cell surface; (2) the virus is internalized into the cell; (3) the M2 ion channel is expressed on the viral surface; (4) the M2 ion channel opens to permit proton entry, leading to a release of viral RNA that enters the nucleus, is replicated and results in viral protein synthesis; and (5) the viral components are packaged into virions and released (6).

The following terms are used herein, the definitions of which are provided for guidance.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

As used herein, the term "attenuated," as used in conjunction with a virus, refers to a virus having reduced virulence or pathogenicity as compared to a non-attenuated counterpart, yet is still viable or live. Typically, attenuation renders an infectious agent, such as a virus, less harmful or virulent to an infected subject compared to a non-attenuated virus. This is in contrast to killed or completely inactivated virus.

As used herein, the terms "effective amount" or "therapeutically effective amount" or "pharmaceutically effective amount" refer to a quantity sufficient to achieve a desired therapeutic and/or prophylactic effect, e.g., an amount which results in the prevention of, disease, condition and/or symptom(s) thereof. In the context of therapeutic or prophylactic applications, the amount of a composition administered to the subject will depend on the type and severity of the disease and on the characteristics of the individual, such as general health, age, sex, body weight and tolerance to the composition drugs. It will also depend on the degree, severity and type of disease or condition. The skilled artisan will be able to determine appropriate dosages depending on these and other factors. In some embodiments, multiple doses are administered. Additionally or alternatively, in some embodiments, multiple therapeutic compositions or compounds (e.g., immunogenic compositions, such as vaccines) are administered.

As used herein, the term "host cell" refers to a cell in which a pathogen, such as a virus, can replicate. In some embodiments, host cells are in vitro, cultured cells. Non-limiting examples of such host cells include, but are not limited to, CHO cells, Vero cells, and MDCK cells. Additionally or alternatively, in some embodiments, host cells are in vivo (e.g., cells of an infected vertebrate, such as an avian or mammal). In some embodiments, the host cells may be modified, e.g., to enhance viral production such as by enhancing viral infection of the host cell and/or by enhancing viral growth rate. By way of example, but not by way of limitation, exemplary host cell modifications include recombinant expression of 2-6-linked sialic acid receptors on the cell surface of the host cell, and/or recombinant expression of a protein in the host cells that has been rendered absent or ineffective in the pathogen or virus.

The term "immunogenic composition" is used herein to refer to a composition that will elicit an immune response in a mammal that has been exposed to the composition. In some embodiments, an immunogenic composition comprises at least one M2-deficient mutant influenza A M2SR strain (e.g., A/California/07/2009 (H1NI) (comprising an M2SR mutant comprising SEQ ID NO: 1, SEQ ID NO: 2, or SEQ ID NO: 3), A/Brisbane/10/2007 (H3N2) (comprising an M2SR mutant comprising SEQ ID NO: 1, SEQ ID NO: 2, or SEQ ID NO: 3). In some embodiments, an immunogenic composition comprises at least one BM2-deficient mutant influenza B BM2SR strain (e.g., B/Brisbane/60/2008 (Victoria) (comprising a BM2SR mutant comprising SEQ ID NO: 6, SEQ ID NO: 7, SEQ ID NO: 8, SEQ ID NO: 9, SEQ ID NO: 10, or SEQ ID NO: 11), B/Wisconsin/01/2010 (Yamagata) (comprising a BM2SR mutant comprising SEQ ID NO: 6, SEQ ID NO: 7, SEQ ID NO: 8, SEQ ID NO: 9, SEQ ID NO: 10, or SEQ ID NO: 11). In some embodiments, an immunogenic composition comprises A/California/07/2009 (H1NI) (comprising an M2SR mutant comprising SEQ ID NO: 1, SEQ ID NO: 2, or SEQ ID NO: 3), A/Brisbane/10/2007 (H3N2) (comprising an M2SR mutant comprising SEQ ID NO: 1, SEQ ID NO: 2, or SEQ ID NO: 3), B/Brisbane/60/2008 (Victoria) (comprising a BM2SR mutant comprising SEQ ID NO: 6, SEQ ID NO: 7, SEQ ID NO: 8, SEQ ID NO: 9, SEQ ID NO: 10, or SEQ ID NO: 11), and B/Wisconsin/01/2010 (Yamagata) (comprising a BM2SR mutant comprising SEQ ID NO: 6, SEQ ID NO: 7, SEQ ID NO: 8, SEQ ID NO: 9, SEQ ID NO: 10, or SEQ ID NO: 11) formulated as a quadrivalent vaccine.

In some embodiments, the immunogenic compositions described herein may be formulated for administration (i.e., formulated for "exposure" to the mammal) in a number of forms. For example, in some embodiments, the immunogenic compositions are prepared for oral, pulmonary, intravenous, intramuscular, subcutaneous, parenteral, nasal, or topical administration. Compositions may also be formulated for specific dosage forms. For example, in some embodiments, the immunogenic composition may be formulated as a liquid, gel, aerosol, ointment, cream, lyophilized formulation, powder, cake, tablet, or capsule. In other embodiments, the immunogenic composition is formulated as a controlled release formulation, delayed release formulation, extended release formulation, pulsatile release formulation, and mixed immediate release formulation. In some embodiments, the immunogenic composition is provided as a liquid. In other embodiments, the immunogenic composition is provided in lyophilized form.

As used herein, the term "infected" refers to harboring a disease or pathogen, such as a virus. An infection can be intentional, such as by administration of a virus or pathogen (e.g., by vaccination), or unintentional, such as by natural transfer of the pathogen from one organism to another, or from a contaminated surface to the organism.

As used herein, the terms "isolated" and/or "purified" refer to in vitro preparation, isolation and/or purification of a nucleic acid (e.g., a vector or plasmid), polypeptide, virus or cell such that it is not associated with unwanted in vivo substances, or is substantially purified from unwanted in vivo substances with which it normally occurs. For example, in some embodiments, an isolated virus preparation is obtained by in vitro culture and propagation, and is substantially free from other infectious agents. As used herein, "substantially free" means below the level of detection for a particular compound, such as unwanted nucleic acids, proteins, cells, viruses, infectious agents, etc. using standard detection methods for that compound or agent.

As used herein the terms "mutant," "mutation," and "variant" are used interchangeably and refer to a nucleic acid or polypeptide sequence which differs from a wild-type sequences. In some embodiments, mutant or variant sequences are naturally occurring. In other embodiments, mutant or variant sequences are recombinantly and/or chemically introduced. In some embodiments, nucleic acid mutations include modifications (e.g., additions, deletions, substitutions) to RNA and/or DNA sequences. In some embodiments, modifications include chemical modification (e.g., methylation) and may also include the substitution or addition of natural and/or non-natural nucleotides. Nucleic acid mutations may be silent mutations (e.g., one or more nucleic acid changes which code for the same amino acid as the wild-type sequence) or may result in a change in the encoded amino acid, result in a stop codon, or may introduce splicing defects or splicing alterations. Nucleic acid mutations to coding sequences may also result in conservative or non-conservative amino acid changes.

As used herein the term "recombinant virus" refers to a virus that has been manipulated in vitro, e.g., using recombinant nucleic acid techniques, to introduce changes to the viral genome and/or to introduce changes to the viral proteins. For example, in some embodiments, recombinant viruses may include both wild-type, endogenous, nucleic acid sequences and mutant and/or exogenous nucleic acid sequences. Additionally or alternatively, in some embodiments, recombinant viruses may include modified protein components, such as mutant or variant matrix, hemagglutinin, neuraminidase, nucleoprotein, non-structural and/or polymerase proteins.

As used herein the term "recombinant cell" or "modified cell" refer to a cell that has been manipulated in vitro, e.g., using recombinant nucleic acid techniques, to introduce nucleic acid into the cell and/or to modify cellular nucleic acids. Examples of recombinant cells includes prokaryotic or eukaryotic cells carrying exogenous plasmids, expression vectors and the like, and/or cells which include modifications to their cellular nucleic acid (e.g., substitutions, mutations, insertions, deletions, etc., into the cellular genome). An exemplary recombinant cell is one which has been manipulated in vitro to stably express an exogenous protein, such as a viral M2 protein.

As used herein the term "single replication (SR) virus" refers to a virus that is defective in a virion protein that functions in viral entry of a host cell or release from a host cell. For example, M2SR, as described herein, belongs to the novel class of single-replication (SR) virus vaccines in contrast to classical live attenuated influenza vaccines. SR viruses are defective in a virion protein that functions in viral entry or release, such as the flu M2 ion channel protein that does not affect viral genome replication but is indispensable for virus growth. In contrast, traditional attenuated live virus vaccines contain multiple mutations in the viral replication machinery resulting in a highly attenuated phenotype. The SR vaccine virus mechanisms therefore do not affect the virus infection kinetics and antigen production in contrast to attenuated live vaccines.

As used herein "subject" and "patient" are used interchangeably and refer to an animal, for example, a member of any vertebrate species. The methods and compositions of the presently disclosed subject matter are particularly useful for warm-blooded vertebrates including mammals and birds. Exemplary subjects may include mammals such as humans, as well as mammals and birds of importance due to being endangered, of economic importance (animals raised on farms for consumption by humans) and/or of social importance (animals kept as pets or in zoos) to humans. In some embodiments, the subject is a human. In some embodiments, the subject is not human.

As used herein, the term "type" and "strain" as used in conjunction with a virus are used interchangeably, and are used to generally refer to viruses having different characteristics. For example, influenza A virus is a different type of virus than influenza B virus. Likewise, influenza A H1N1 is a different type of virus than influenza A H2N1, H2N2 and H3N2. Additionally or alternatively, in some embodiments, different types of virus such as influenza A H2N1, H2N2 and H3N2 may be termed "subtypes."

The term "vaccine" is used herein to refer to a composition that is administered to a subject to produce or increase immunity to a particular disease. In some embodiments, vaccines include a pharmaceutically acceptable adjuvant and/or a pharmaceutically acceptable carrier.

As used herein, the term "vRNA" refers to the RNA comprising a viral genome, including segmented or non-segmented viral genomes, as well as positive and negative strand viral genomes. vRNA may be wholly endogenous and "wild-type" and/or may include recombinant and/or mutant sequences.

The term "virulence" is used herein to refer to the relative ability of a pathogen to cause disease.

The term "attenuated virulence" or "reduced virulence" is used herein to refer to a reduced relative ability of a pathogen to cause disease. For example, attenuated virulence or reduced virulence can describe viruses that have been weakened so they produce immunity when exposed to a subject, but do not cause disease, or cause a less severe form, duration, onset or later onset of the disease.

As used herein, "M2SR" refers to a single-replication (SR) M2-deficient recombinant influenza virus. Exemplary M2SR influenza viruses described herein comprise SEQ ID NO: 1, SEQ ID NO: 2, and/or SEQ ID NO: 3, a virus comprising SEQ ID NO: 1, SEQ ID NO: 2, and/or SEQ ID NO: 3, or a vaccine comprising a virus comprising SEQ ID NO: 1, SEQ ID NO: 2, and/or SEQ ID NO: 3, depending on the context in which it is used. For example, in describing mutations of the M2 gene demonstrated herein, "M2SR" refers to SEQ ID NO: 1, SEQ ID NO: 2, and/or SEQ ID NO: 3. In particular, "M2SR-1" refers to SEQ ID NO: 1; "M2SR-2" refers to SEQ ID NO: 2; and "M2SR-3" refers to SEQ ID NO: 3. When describing the viral component of a vaccine, "M2SR" refers to a recombinant influenza virus that does not express functional M2 protein. When describing a vaccine, "M2SR" refers to a vaccine comprising the M2SR recombinant virus.

As used herein, "M2SR virus" encompasses a recombinant influenza virus that does not express functional M2 protein. In some embodiments, the M2SR virus comprises genes of other influenza viruses. In some embodiments, the virus comprises the HA and NA genes of Influenza A/Brisbane/10/2007-like A/Uruguay/716/2007(H3N2). In some embodiments, the M2SR virus comprises the HA and NA genes of the A/California/07/2009 (CA07) (H1N1pdm) virus.

As used herein, "BM2SR" refers to a single-replication (SR) BM2-deficient recombinant influenza virus. Exemplary BM2SR influenza viruses described herein comprise SEQ ID NO: 6, SEQ ID NO: 7, SEQ ID NO: 8, SEQ ID NO: 9, SEQ ID NO: 10, and/or SEQ ID NO: 11, a virus comprising SEQ ID NO: 6, SEQ ID NO: 7, SEQ ID NO: 8, SEQ ID NO: 9, SEQ ID NO: 10, and/or SEQ ID NO: 11, or a vaccine comprising a virus comprising SEQ ID NO: 6, SEQ ID NO: 7, SEQ ID NO: 8, SEQ ID NO: 9, SEQ ID NO: 10, and/or SEQ ID NO: 11, depending on the context in which it is used. For example, in describing mutations of the BM2 gene demonstrated herein, "BM2SR" refers to SEQ ID NO: 6, SEQ ID NO: 7, SEQ ID NO: 8, SEQ ID NO: 9, SEQ ID NO: 10, and/or SEQ ID NO: 11. In particular, "BM2SR-1" refers to SEQ ID NO: 6; "BM2SR-2" refers to SEQ ID NO: 7; "BM2SR-3" refers to SEQ ID NO: 8; "BM2SR-4" refers to SEQ ID NO: 9; "BM2SR-5" refers to SEQ ID NO: 10; and "BM2SR-0" refers to SEQ ID NO: 11. When describing the viral component of a vaccine, "BM2SR" refers to a recombinant influenza virus which by way of example, but not by way of limitation, possesses internal genes of B/Lee/40 (nucleoprotein (NP), polymerase genes (PA, PB1, PB2), non-structural (NS1 and NS2), NB, matrix (BM1)), but which does not express functional BM2 protein. When describing a vaccine, "BM2SR" refers to a vaccine comprising the BM2SR recombinant virus.

As used herein, "BM2SR virus" encompasses a recombinant influenza virus which possesses internal genes of B/Lee/40 (nucleoprotein (NP), polymerase genes (PA, PB 1, PB2), non-structural (NS1 and NS2), matrix (BM1)), but which does not express functional BM2 protein, alone or in combination with other viral components and/or genes encoding other viral components. In some embodiments, the BM2SR virus comprises genes of other influenza viruses. In some embodiments, the virus comprises the HA and NA genes of Influenza B/Brisbane/60/2008-like B/Brisbane/60/2008 (B Victoria lineage). In some embodiments, the M2SR virus comprises the HA and NA genes of the B/Wisconsin/1/2010-like (B Yamagata lineage) virus. In some embodiments, the BM2SR virus possesses internal genes (NP, PA, PB1, PB2, NS1 and NS2, BM1) of recent influenza B viruses.

II. Influenza A virus and influenza B virus

A. General

Influenza is a leading cause of death among American adults. The causal agent of influenza are viruses of the family Orthomyxoviridae including influenza A virus, influenza B virus, and influenza C virus.

The influenza A virus is an enveloped, negative-strand RNA virus. The genome of influenza A virus is contained on eight single (non-paired) RNA strands the complements of which code for eleven proteins (HA, NA, NP, M1, M2, NS1, NEP, PA, PB1, PB1-F2, PB2). The total genome size is about 14,000 bases. The segmented nature of the genome allows for the exchange of entire genes between different viral strains during cellular cohabitation. The eight RNA segments are as follows. 1) HA encodes hemagglutinin (about 500 molecules of hemagglutinin are needed to make one virion); 2) NA encodes neuraminidase (about 100 molecules of neuraminidase are needed to make one virion); 3) NP encodes nucleoprotein; 4) M encodes two proteins (the M1 and the M2) by using different reading frames from the same RNA segment (about 3000 M1 molecules are needed to make one virion); 5) NS encodes two proteins (NS 1 and NEP) by using different reading frames from the same RNA segment; 6) PA encodes an RNA polymerase; 7) PB 1 encodes an RNA polymerase and PB 1-F2 protein (induces apoptosis) by using different reading frames from the same RNA segment; 8) PB2 encodes an RNA polymerase.

The influenza B virus is also an enveloped, negative-strand RNA virus. The genome of influenza B virus is contained on eight single (non-paired) RNA strands the complements of which code for eleven proteins. Of these proteins, nine are also found in influenza A virus: three RNA-dependent RNA polymerase subunits (PB 1, PB2, and PA), hemagglutinin (HA), nucleoprotein (NP), neuraminidase (NA), matrix protein (M1 or BM1), and two non-structural proteins (NS1 and NS2, also known as NEP). Two proteins, NB and BM2, are unique to influenza B virus. The total genome size is about 14,500 bases. The segmented nature of the genome allows for the exchange of entire genes between different viral strains during cellular cohabitation, a process known as reassortment. The eight RNA segments, numbered in order of decreasing length, are as follows. Segments 1, 2, and 3 encode PB1, PB2, and PA, respectively, which are RNA polymerase subunits. Segment 4 encodes HA (hemagglutinin). Segment 5 encodes NP (nucleoprotein). Segment 6 encodes both NB (NB protein, the function of which is unknown) and NA (neuraminidase). Segment 7 encodes both BM1 (matrix protein) and BM2 (ion channel) by a bicistronic mRNA, the translational strategy of which is unique. The BM2 initiation codon overlaps with the BM1 termination codon (TAATG, a stop-start pentanucleotide motif). The BM2 protein is translated by this stop-start translational mechanism unlike the M2 protein of influenza A virus, which is translated from a spliced mRNA. Segment 8 encodes both NS1 and NEP by using different reading frames from the same RNA segment.

Both influenza A and B evolve antigenically over time by the process of antigenic drift, in which mutations to hemagglutinin (HA) protein allow viruses to escape existing human immunity and persist in the human population. There are several subtypes of influenza A, named according to an H number (for the type of hemagglutinin) and an N number (for the type of neuraminidase). Currently, there are 16 different H antigens known (H1 to H16) and nine different N antigens known (N1 to N9). Each virus subtype has mutated into a variety of strains with differing pathogenic profiles; some pathogenic to one species but not others, some pathogenic to multiple species. Exemplary Influenza A virus subtypes that have been confirmed in humans, include, but are not limited to H1N1 which caused the "Spanish Flu" and the 2009 swine flu outbreak; H2N2 which caused the "Asian Flu" in the late 1950s; H3N2 which caused the Hong Kong Flu in the late 1960s; H5N1, considered a global influenza pandemic threat through its spread in the mid-2000s; H7N7; H1N2 which is currently endemic in humans and pigs; and H9N2, H7N2, H7N3, H5N2, H 10N7.

Two antigenically and genetically distinct lineages of influenza B viruses have co-circulated and caused disease in humans since at least 1988. Influenza viruses of the Victoria lineage were the predominant type B strains circulating worldwide in the 1980s with the Yamagata lineage becoming the dominant type B virus in the early 1990s. Since 1991, Victoria lineage viruses have been isolated infrequently and been limited almost entirely to eastern Asia. Victoria viruses reemerged in 2002 and both Yamagata and Victoria lineages have coexisted since.

Evolutionary relationships of influenza B viruses isolated from 1940 to 2016 indicate that the BM1 and BM2 proteins of modern isolates are more closely related to each other than to B/Lee/40.

Influenza viruses have a standard nomenclature that includes virus type; species from which it was isolated (if non-human); location at which it was isolated; isolate number; isolate year; and, for influenza A viruses only, HA and NA subtype. Thus, B/Yamagata/16/88 was isolate number 16 of a human influenza B virus taken in Yamagata (Japan) in 1988.

Some influenza A variants are identified and named according to the known isolate to which they are most similar, and thus are presumed to share lineage (e.g., Fujian flu virus-like); according to their typical host (example Human flu virus); according to their subtype (example H3N2); and according to their pathogenicity (example LP, Low Pathogenic). Thus, a flu from a virus similar to the isolate A/Fujian/411/2002(H3N2) can be called Fujian flu, human flu, and H3N2 flu.

In addition, influenza variants are sometimes named according to the species (host) the strain is endemic in or adapted to. The main variants named using this convention are: bird flu, human flu, swine influenza, equine influenza and canine influenza. Variants have also been named according to their pathogenicity in poultry, especially chickens, e.g., Low Pathogenic Avian Influenza (LPAI) and Highly Pathogenic Avian Influenza (HPAI).

B. Life cycle and structure

The life cycle of influenza viruses generally involves attachment to cell surface receptors, entry into the cell and uncoating of the viral nucleic acid, followed by replication of the viral genes inside the cell. After the synthesis of new copies of viral proteins and genes, these components assemble into progeny virus particles, which then exit the cell. Different viral proteins play a role in each of these steps.

The influenza A particle is made up of a lipid envelope which encapsulates the viral core. The inner side of the envelope is lined by the matrix protein (M1), while the outer surface is characterized by two types of glycoprotein spikes: hemagglutinin (HA) and neuraminidase (NA). M2, a transmembrane ion channel protein, is also part of the lipid envelope. See e.g., FIG. 1. The influenza B particle comprises a similar structure.

The HA protein, a trimeric type I membrane protein, is responsible for binding to sialyloligosaccharides (oligosaccharides containing terminal sialic acid linked to galactose) on host cell surface glycoproteins or glycolipids. This protein is also responsible for fusion between viral and host cell membranes, following virion internalization by endocytosis.

Neuraminidase (NA), a tetrameric type II membrane protein, is a sialidase that cleaves terminal sialic acid residues from the glycoconjugates of host cells and the HA and NA, and thus is recognized as receptor-destroying enzyme. This sialidase activity is necessary for efficient release of progeny virions from the host cell surface, as well as prevention of progeny aggregation due to the binding activity of viral HAs with other glycoproteins. Thus, the receptor-binding activity of the HA and the receptor-destroying activity of the NA likely act as counterbalances, allowing efficient replication of influenza.

The genome segments are packaged into the core of the viral particle. The RNP (RNA plus nucleoprotein, NP) is in helical form with three viral polymerase polypeptides associated with each segment.

The influenza virus life cycle begins with binding of the HA to sialic acid-containing receptors on the surface of the host cell, followed by receptor-mediated endocytosis (FIG. 1). The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerise complex, which is formed by the PA, PB1, and PB2 proteins. RNPs are transported into the nucleus, where transcription and replication take place. The RNA polymerise complex catalyzes three different reactions: (1) synthesis of an mRNA with a 5' cap and 3' polyA structure, (2) a full-length complementary RNA (cRNA), and (3) genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a role late in infection by removing sialic acid from sialyloligosaccharides, thus releasing newly assembled virions from the cell surface and preventing the self-aggregation of virus particles. Although virus assembly involves protein-protein and protein-vRNA interactions, the nature of these interactions remains largely unknown.

C. Role of the M2 and BM2 protein

As described above, spanning the influenza A viral membrane are three proteins: hemagglutinin (HA), neuramimidase (NA), and M2. The extracellular domains (ectodomains) of HA and NA are quite variable, while the ectodomain domain of M2 is essentially invariant among influenza A viruses. The M2 ion channel protein does not affect viral genome replication but is indispensable for virus growth. Single replication (SR) viruses are defective in a virion protein that functions in viral entry or release, such as the influenza A M2 or influenza BM2 ion channel protein. In contrast, traditional attenuated live virus vaccines contain multiple mutations in the viral replication machinery resulting in a highly attenuated phenotype. Without wishing to be bound by theory, in influenza A viruses, the M2 protein, which possesses ion channel activity, is thought to function at an early state in the viral life cycle between host cell penetration and un-coating of viral RNA. Once virions have undergone endocytosis, the virion-associated M2 ion channel, a homotetrameric helix bundle, is believed to permit protons to flow from the endosome into the virion interior to disrupt acid-labile M1 protein-ribonucleoprotein complex (RNP) interactions, thereby promoting RNP release into the cytoplasm. In addition, among some influenza strains whose HAs are cleaved intracellularly (e.g., A/fowl plagues/Rostock/34), the M2 ion channel is thought to raise the pH of the trans-Golgi network, preventing conformational changes in the HA due to conditions of low pH in this compartment. It was also shown that the M2 transmembrane domain itself can function as an ion channel. M2 protein ion channel activity is thought to be essential in the life cycle of influenza viruses, because amantadine hydrochloride, which blocks M2 ion channel activity, has been shown to inhibit viral replication. However, a requirement for this activity in the replication of influenza A viruses has not been directly demonstrated. The functional counterpart to the influenza A virus M2 protein in influenza B viruses is the type III transmembrane protein known as BM2.

D. M2 and BM2 viral mutants as vaccines

M2SR belongs to the novel class of single-replication (SR) virus vaccines. SR viruses are defective in a virion protein that functions in viral entry or release, such as the flu M2 ion channel protein, that do not affect viral genome replication but are indispensable for virus growth. In contrast, traditional live attenuated vaccines contain multiple mutations in the viral replication machinery resulting in a highly attenuated phenotype. The two different vaccine virus mechanisms therefore affect the virus infection kinetics and antigen production, which affect protection and induction of immune responses. Replication-defective viruses provide unique forms of viral vaccines that combine the safety of an inactivated virus vaccine and the immunogenicity of a live virus vaccine by expressing viral gene products within cells so the antigens can be presented efficiently by both MHC class I and class II pathways. Single replication viruses can also activate Toll-like receptors and other innate immune response pathways, thereby serving as their own adjuvants. In addition, these viruses can be used as tools to probe the function of the immune system. These mutant viruses are defective in a virion protein that functions after viral assembly. The viruses are propagated in complementing cells that express the missing gene product. In normal cells, the replication cycle occurs normally and progeny virions are produced. However, these virions are noninfectious so the infection does not spread to a second round of cells.

III. M2 and BM2 viral mutants

In one aspect, influenza A viruses harboring a mutant M2 vRNA sequence are disclosed. Typically, such mutants do not have M2 ion channel activity, exhibit attenuated growth properties in vivo, cannot produce infectious progeny and are non-pathogenic or show reduced pathogenesis in infected subjects. In another aspect, influenza B viruses harboring a mutant BM2 vRNA sequence are disclosed. Typically, such mutants do not have BM2 ion channel activity, exhibit attenuated growth properties in vivo, cannot produce infectious progeny and are non-pathogenic or show reduced pathogenesis in infected subjects. The mutant viruses are immunogenic, and when used as a vaccine, provide protection against infection with a counterpart wild-type and/or other pathogenic virus. Additionally, the M2 and BM2 mutants disclosed herein are stable, and do not mutate to express a functional M2 or BM2 polypeptide, regardless of the host cell used. Additionally or alternatively, in some embodiments, the M1 protein of these mutants is produced without detectable alteration to its function. In some embodiments, viruses harboring the mutant M2 or BM2 nucleic acid sequences cannot replicate in a host cell in which a corresponding wild-type virus could be propagated. By way of example, but not by way of limitation, in some embodiments, the wild-type virus can be grown, propagated and replicate in culturing MDCK cells, CHO cells and/or Vero cells, while the corresponding virus harboring a mutant M2 or BM2 sequence cannot grow, replicate or be propagated in the same type of cells.

As noted above, in some embodiments, the M2 or BM2 mutant virus is stable, and does not mutate or revert to wild-type or to a non-wild-type sequence encoding a functional M2 or BM2 protein in a host cell. For example, in some embodiments, the M2 or BM2 mutant virus is stable for 2 passages, 3 passages, 5 passages, 10 passages, 12 passages, 15 passages, 20 passages, 25 passages or more than 25 passages in a host cell. In some embodiments, the host cell is an unmodified host cell. In some embodiments, the host cell is any mammalian cell stably providing M2 in trans. In other embodiments, the host cell is a modified host cell, such as a MDCK or Vero cell which expresses the M2 or BM2 protein.

In some embodiments, the M2 or BM2 mutants include one or more nucleic acid substitutions and/or deletions. In some embodiments, the mutations are localized in nucleic acids which code for one or more of the extracellular domain of the M2 or BM2 protein, the transmembrane domain of the M2 or BM2 proteins, and/or the cytoplasmic tail of the M2 or BM2 protein. Additionally or alternatively, in some embodiments, one or more nucleic acid mutations results in a splice variant, one or more stop codons and/or one or more amino acid deletions of the M2 or BM2 peptide. In some embodiments, viruses carrying the mutant M2 or BM2 nucleic acid produce a non-functional M2 or BM2 polypeptide. In some embodiments, viruses carrying the mutant M2 or BM2 nucleic acid do not produce an M2 or BM2 polypeptide. In some embodiments, viruses carrying the mutant M2 or BM2 nucleic acid produce a truncated M2 or BM2 polypeptide.

Three exemplary, non-limiting M2 viral mutants (M2SR-1, M2SR-2 and M2SR-3) are provided below in Tables 1-3. In the tables, lower case letters correspond to the M2 sequence; upper case letters correspond to the M1 sequence and non-coding regions; mutant sequence (e.g., stop codons, splice defect) are in bold, underlined. Underlined (lower case) bases in the M2SR-2 mutant indicate the region deleted in the M2SR-1 and M2SR-3 mutants. Lower case italicized bases include M and M2 overlap regions.

TABLE 1

M2SR-1 (SEQ ID NO: 1) M2 ectodomain + 2 stop codons + TM deletion (PR8 M segment + 2 stops (786-791) without 792-842 (TM)).

3'AGCAAAAG

TABLE 4-continued

M1/M2 wild-type nucleic acid sequence (SEQ ID NO: 5)

```
TACAACAGGATGGGGGCTGTGACCACTGAAGTGGC
ATTTGGCCTGGTATGTGCAACCTGTGAACAGATTG
CTGACTCCCAGCATCGGTCTCATAGGCAAATGGTG
ACAACAACCAATCCACTAATCAGACATGAGAACAG
AATGGTTTTAGCCAGCACTACAGCTAAGGCTATGG
AGCAAATGGCTGGATCGAGTGAGCAAGCAGCAGAG
GCCATGGAGGTTGCTAGTCAGGCTAGACAAATGGT
GCAAGCGATGAGAACCATTGGGACTCATCCTAGCT
CCAGTGCTGGTCTGAAAAATGATCTTCTTGAAAAT
TTGCAGgcctatcagaaacgaatgggggtgcagat
gcaacggttcaagtgatcctctcactattgccgca
```

TABLE 4-continued

M1/M2 wild-type nucleic acid sequence (SEQ ID NO: 5)

```
aatatcattgggatcttgcacttgacattgtggat
tcttgatcgtctttttttcaaatgcatttaccgtc
gctttaaatacggactgaaaggagggccttctacg
gaaggagtgccaaagtctatgagggaagaatatcg
aaaggaacagcagagtgctgtggatgctgacgatg
gtcattttgtcagcatagagctggagtaaAAAACT
ACCTTGTTTCTACT
```

Exemplary, non-limiting BM2SR viral mutants (BM2SR-1, BM2SR-2, BM2SR-3, BM2SR-4, BM2SR-5, and BM2SR-0) are provided below in Table 5.

TABLE 5

BM2SR Sequences
M segment 7 sequences of BM2SR influenza viruses containing null mutations in BM2 genes.

```
BM2SR-1 (SEQ ID NO: 6) influenza
B/FL/4/2006 Segment 7 with intact BM1 + total
BM2 deletion of 329 bp (indicated by -)
(mRNA sense).
5'AGCAGAAGCACGCACTTTCTTAAAATGTCGCTGTTTGGAGACACAATTGCCT
ACCTGCTTTCATTGACAGAAGATGGAGAAGGCAAAGCAGAACTAGCAGAAAA
ATTACACTGTTGGTTCGGTGGGAAAGAATTTGACCTAGACTCTGCCTTGGAATG
GATAAAAAACAAAGATGCTTAACTGACATACAGAAAGCACTAATTGGCGCCT
CTATCTGCTTTTTAAAACCCAAAGACCAGGAAAGAAAAAGAAGATTCATCACA
GAGCCCCTATCAGGAATGGGGACAACAGCAACAAAAAAGAAGGGCCTGATTC
TAGCTGAGAGAAAAATGAGAAGATGTGTGAGCTTCCATGAAGCATTTGAAATA
GCAGAAGGCCATGAAAGCTCAGCGTTACTATATTGTCTCATGGTCATGTACCTG
AATCCTGGAAATTATTCAATGCAAGTAAAACTAGGAACGCTCTGTGCTTTGTGC
GAAAAACAAGCATCACATTCACACAGGGCTCATAGCAGAGCAGCGAGATCTTC
AGTGCCTGGAGTGAGACGGGAAATGCAGATGGTCTCAGCTATGAACACAGCA
AAAACAATGAATGGAATGGGAAAAGGAGAAGACGTTCAAAAACTGGCAGAAG
AACTGCAAAGCAACATTGGAGTATTGAGATCTCTTGGGGCAAGTCAAAAGAAT
GGGGAAGGAATTGCAAAGGATGTAATGGAAGTGCTAAAGCAGAGCTCTATGG
GAAATTCAGCTCTTGTGAAGAAATACCTATAA
------------------------------------------------
------------------------------------------------
------------------------------------------------
------------------------------------------------
------------------------------------------------
------------------------------------------------
-------------------------------
ATTCAATTTTTACTGTACTTCTTACTATGCATTTAAGCAAATTGTAATCAATGTC
AGCAAATAAACTGGAAAAAGTGCGTTGTTTCTACT
BOLD UPPER CASE = BM1 ORF Stop Codon
- = designates deleted nucleotides BM2SR-2 (SEQ ID NO: 7) influenza B/FL/4/2006
Segment 7 with intact BM1 + partial
BM2 deletion of 296 bp (indicated by -) +
insertion of stop codons in 3 frames. (mRNA
sense).
5'AGCAGAAGCACGCACTTTCTTAAAATGTCGCTGTTTGGAGACACAATTGCCT
ACCTGCTTTCATTGACAGAAGATGGAGAAGGCAAAGCAGAACTAGCAGAAAA
ATTACACTGTTGGTTCGGTGGGAAAGAATTTGACCTAGACTCTGCCTTGGAATG
GATAAAAAACAAAGATGCTTAACTGACATACAGAAAGCACTAATTGGCGCCT
CTATCTGCTTTTTAAAACCCAAAGACCAGGAAAGAAAAAGAAGATTCATCACA
GAGCCCCTATCAGGAATGGGGACAACAGCAACAAAAAAGAAGGGCCTGATTC
TAGCTGAGAGAAAAATGAGAAGATGTGTGAGCTTCCATGAAGCATTTGAAATA
GCAGAAGGCCATGAAAGCTCAGCGTTACTATATTGTCTCATGGTCATGTACCTG
AATCCTGGAAATTATTCAATGCAAGTAAAACTAGGAACGCTCTGTGCTTTGTGC
GAAAAACAAGCATCACATTCACACAGGGCTCATAGCAGAGCAGCGAGATCTTC
AGTGCCTGGAGTGAGACGGGAAATGCAGATGGTCTCAGCTATGAACACAGCA
AAAACAATGAATGGAATGGGAAAAGGAGAAGACGTTCAAAAACTGGCAGAAG
AACTGCAAAGCAACATTGGAGTATTGAGATCTCTTGGGGCAAGTCAAAAGAAT
GGGGAAGGAATTGCAAAGGATGTAATGGAAGTGCTAAAGCAGAGCTCTATGG
GAAATTCAGCTCTTGTGAAGAAATACCTATAATGCTCGAACCATTTCAGATTCT
TTCAATTTGTtagAtagC-----------------------------------
------------------------------------------------
------------------------------------------------
------------------------------------------------
------------------------------------------------
------------------------------------
```

TABLE 5-continued

BM2SR Sequences
M segment 7 sequences of BM2SR influenza
viruses containing null mutations in BM2
genes.

taaATTCAATTTTTACTGTACTTCTTACTATGCATTTAAGCAAATTGTAATCAATG
TCAGCAAATAAACTGGAAAAAGTGCGTTGTTTCTACT
BOLD UPPER CASE = BM1 ORF Stop Codon
bold lower case= Inserted BM2 Stop Codons
- = designates deleted nucleotides BM2SR-3 (SEQ ID NO: 8) influenza B/FL/4/2006
Segment 7 with intact BM1 + BM1
M86V mutation + partial BM2 deletion of 296 bp
(indicated by -) + insertion of stop
codons in 3 frames. (mRNA sense).
5'AGCAGAAGCACGCACTTTCTTAAAATGTCGCTGTTTGGAGACACAATTGCCT
ACCTGCTTTCATTGACAGAAGATGGAGAAGGCAAAGCAGAACTAGCAGAAAA
ATTACACTGTTGGTTCGGTGGGAAAGAATTTGACCTAGACTCTGCCTTGGAATG
GATAAAAAACAAAAGATGCTTAACTGACATACAGAAAGCACTAATTGGCGCCT
CTATCTGCTTTTTAAAACCCAAAGACCAGGAAAGAAAAAGAAGATTCATCACA
GAGCCCCTATCAGGAgTGGGGACAACAGCAACAAAAAAGAAGGGCCTGATTC
TAGCTGAGAGAAAAATGAGAAGATGTGTGAGCTTCCATGAAGCATTTGAAATA
GCAGAAGGCCATGAAAGCTCAGCGTTACTATATTGTCTCATGGTCATGTACCTG
AATCCTGGAAATTATTCAATGCAAGTAAAACTAGGAACGCTCTGTGCTTTGTGC
GAAAAACAAGCATCACATTCACACAGGGCTCATAGCAGAGCAGCGAGATCTTC
AGTGCCTGGAGTGAGACGGGAAATGCAGATGGTCTCAGCTATGAACACAGCA
AAAACAATGAATGGAATGGGAAAAGGAGAAGACGTTCAAAAACTGGCAGAAG
AACTGCAAAGCAACATTGGAGTATTGAGATCTCTTGGGGCAAGTCAAAAGAAT
GGGGAAGGAATTGCAAAGGATGTAATGGAAGTGCTAAAGCAGAGCTCTATGG
GAAATTCAGCTCTTGTGAAGAAATACCTATAATGCTCGAACCATTTCAGATTCT
TTCAATTTGTtagAtagC‐‐‐‐‐‐‐‐‐‐‐‐‐‐‐‐‐‐‐‐‐‐‐‐‐‐‐‐‐‐‐‐‐‐‐‐‐
‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐
‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐
‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐
‐‐‐‐‐‐‐‐‐‐‐‐‐‐‐‐‐‐‐‐‐‐‐‐‐‐‐‐‐‐‐‐‐‐‐‐‐‐
taaATTCAATTTTTACTGTACTTCTTACTATGCATTTAAGCAAATTGTAATCAATG
TCAGCAAATAAACTGGAAAAAGTGCGTTGTTTCTACT
Bold Underline Mixed Case = BM1 M86V Mutation Codon
BOLD UPPER CASE = BM1 ORF Stop Codon
UNDERLINE UPPERCASE = BM2 ORF remnant
bold lower case= Inserted BM2 Stop Codons
- = designates deleted nucleotides BM2SR-4 (SEQ ID NO: 9) influenza B/FL/4/2006
Segment 7 with intact BM1 + partial
BM2 deletion of 90 bp (indicated by -) + insertion
of 3 stop codons in 3 frames. (mRNA
sense).
5'AGCAGAAGCACGCACTTTCTTAAAATGTCGCTGTTTGGAGACACAATTGCCT
ACCTGCTTTCATTGACAGAAGATGGAGAAGGCAAAGCAGAACTAGCAGAAAA
ATTACACTGTTGGTTCGGTGGGAAAGAATTTGACCTAGACTCTGCCTTGGAATG
GATAAAAAACAAAAGATGCTTAACTGACATACAGAAAGCACTAATTGGCGCCT
CTATCTGCTTTTTAAAACCCAAAGACCAGGAAAGAAAAAGAAGATTCATCACA
GAGCCCCTATCAGGAATGGGACAACAGCAACAAAAAAGAAGGGCCTGATTC
TAGCTGAGAGAAAAATGAGAAGATGTGTGAGCTTCCATGAAGCATTTGAAATA
GCAGAAGGCCATGAAAGCTCAGCGTTACTATATTGTCTCATGGTCATGTACCTG
AATCCTGGAAATTATTCAATGCAAGTAAAACTAGGAACGCTCTGTGCTTTGTGC
GAAAAACAAGCATCACATTCACACAGGGCTCATAGCAGAGCAGCGAGATCTTC
AGTGCCTGGAGTGAGACGGGAAATGCAGATGGTCTCAGCTATGAACACAGCA
AAAACAATGAATGGAATGGGAAAAGGAGAAGACGTTCAAAAACTGGCAGAAG
AACTGCAAAGCAACATTGGAGTATTGAGATCTCTTGGGGCAAGTCAAAAGAAT
GGGGAAGGAATTGCAAAGGATGTAATGGAAGTGCTAAAGCAGAGCTCTATGG
GAAATTCAGCTCTTGTGAAGAAATACCTATAATGCTCGAACCATTTCAGATTCT
TTCAATTTGTtagAtagCtaa‐‐‐‐‐‐‐‐‐‐‐‐‐‐‐‐‐‐‐‐‐‐‐‐‐‐‐‐‐‐‐
‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐‐
‐
AAGGGGCCAAATAAAGAGACAATAAACAGAGAGGTATCAATTTTGAGACACA
GTTACCAAAAAGAAATCCAGGCCAAAGAAGCAATGAAGGAAGTACTCTCTGA
CAACATGGAGGTATTGAGTGACCACATAGTAATTGAGGGGCTTTCTGCTGAAG
AGATAATAAAAATGGGTGAAACAGTTTTGGAGGTAGAAGAATTGCATTAAATT
CAATTTTTACTGTACTTCTTACTATGCATTTAAGCAAATTGTAATCAATGTCAG
CAAATAAA-CTGGAAAAAGTGCGTTGTTTCTACT
BOLD UPPER CASE = BM1 ORF Stop Codon
UNDERLINE UPPERCASE = BM2 ORF remnant
BOLD UNDERLINE UPPERCASE = BM2 ORF Stop Codon
bold lower case= Inserted BM2 Stop Codons
- = designates deleted nucleotides TABLE 5-continued BM2SR Sequences
M segment 7 sequences of BM2SR influenza
viruses containing null mutations in BM2
genes.

BM2SR-5 (SEQ ID NO: 10) influenza B/FL/4/2006
Segment 7 with intact BM1 + BM1
M86V mutation + partial BM2 deletion of 90 bp
(indicated by -) + insertion of 3 stop
codons in 3 frames. (mRNA sense).
5'AGCAGAAGCACGCACTTTCTTAAAATGTCGCTGTTTGGAGACACAATTGCCT
ACCTGCTTTCATTGACAGAAGATGGAGAAGGCAAAGCAGAACTAGCAGAAAA
ATTACACTGTTGGTTCGGTGGGAAAGAATTTGACCTAGACTCTGCCTTGGAATG
GATAAAAAACAAAAGATGCTTAACTGACATACAGAAAGCACTAATTGGCGCCT
CTATCTGCTTTTTAAAACCCAAAGACCAGGAAAGAAAAAGAAGATTCATCACA
GAGCCCCTATCAGGAgTGGGGACAACAGCAACAAAAAAGAAGGGCCTGATTC
TAGCTGAGAGAAAAATGAGAAGATGTGTGAGCTTCCATGAAGCATTTGAAATA
GCAGAAGGCCATGAAAGCTCAGCGTTACTATATTGTCTCATGGTCATGTACCTG
AATCCTGGAAATTATTCAATGCAAGTAAAACTAGGAACGCTCTGTGCTTTGTGC
GAAAAACAAGCATCACATTCACACAGGGCTCATAGCAGAGCAGCGAGATCTTC
AGTGCCTGGAGTGAGACGGGAAATGCAGATGGTCTCAGCTATGAACACAGCA
AAAACAATGAATGGAATGGGAAAAGGAGAAGACGTTCAAAAACTGGCAGAAG
AACTGCAAAGCAACATTGGAGTATTGAGATCTCTTGGGGCAAGTCAAAAGAAT
GGGGAAGGAATTGCAAAGGATGTAATGGAAGTGCTAAAGCAGAGCTCTATGG
GAAATTCAGCTCTTGTGAAGAAATACCTATAATGCTCGAACCATTTCAGATTCT
TTCAATTTGTtagAtagCtaa---------------------------------
---------------------------------------------------------
-
AAGGGGCCAAATAAAGAGACAATAAACAGAGAGGTATCAATTTTGAGACACA
GTTACCAAAAAGAAATCCAGGCCAAAGAAGCAATGAAGGAAGTACTCTCTGA
CAACATGGAGGTATTGAGTGACCACATAGTAATTGAGGGGCTTTCTGCTGAAG
AGATAATAAAAATGGGTGAAACAGTTTTGGAGGTAGAAGAATTGCATTAAATT
CAATTTTTACTGTACTTCTTACTATGCATTTAAGCAAATTGTAATCAATGTCAG
CAAATAAA-CTGGAAAAAGTGCGTTGTTTCTACT
Bold Underline Mixed Case = BM1 M86V Mutation Codon
BOLD UPPER CASE = BM1 ORF Stop Codon
UNDERLINE UPPERCASE = BM2 ORF remnant
bold lower case= Inserted BM2 Stop Codons
BOLD UNDERLINE UPPERCASE = BM2 ORF Stop Codon
- = designates deleted nucleotides BM2SR-O (SEQ ID NO: 11)) influenza B/Lee/1940
Segment 7 with intact BM1 + total
BM2 deletion of 329 bp (indicated by -) (mRNA sense).
5'AGCAGAAGCACGCACTTTCTTAAAATGTCGCTGTTTGGAGACACAATTGCCT
ACCTGCTTTCACTAATAGAAGATGGAGAAGGCAAAGCAGAACTAGCTGAAAA
ATTACACTGTTGGTTCGGTGGGAAAGAATTTGACCTAGATTCTGCTTTGGAATG
GATAAAAAACAAAAGGTGCCTAACTGATATACAAAAAGCACTAATTGGTGCCT
CTATATGCTTTTTAAAACCCAAAGACCAAGAAAGAAAAAGGAGATTCATCACA
GAGCCCCTGTCAGGAATGGGAACAACAGCAACAAAGAAGAAAGGCCTAATTC
TAGCTGAGAGAAAAATGAGAAGATGTGTAAGCTTTCATGAAGCATTTGAAATA
GCAGAAGGCCACGAAAGCTCAGCATTACTATATTGTCTTATGGTCATGTACCTA
AACCCTGAAAACTATTCAATGCAAGTAAAACTAGGAACGCTCTGTGCTTTATG
CGAGAAACAAGCATCGCACTCGCATAGAGCCCATAGCAGAGCAGCAAGGTCTT
CGGTACCTGGAGTAAGACGAGAAATGCAGATGGTTTCAGCTATGAACACAGCA
AAGACAATGAATGGAATGGGAAGGGAGAAGACGTTCCAAAAACTAGCAGAAG
AGCTGCAAAACAACATTGGAGTGTTGAGATCTCTAGGAGCAAGTCAAAAGAAT
GGAGAAGGAATTGCCAAAGATGTAATGGAAGTGCTAAAACAGAGCTCTATGG
GAAATTCAGCTCTTGTGAGGAAATACTTATAA---------------------
---------------------
---------------------------------------------------------
---------------------------------------------------------
---------------------------------------------------------
---------------------------------------------------------
---------------------------------------------------------
-----------
GCCCAATTTTCACTGTATTTCTTACTATGCATTTAAGCAAATTGTAATCAATGTC
AGTGAATAAAACTGGAAAAAGTGCGTTGTTTCTACT
BOLD UPPER CASE = BM1 ORF Stop Codon
- = designates deleted nucleotides The influenza B genomic segment 7 expresses two major polypeptides that are required by the virus for replication, the BM1 matrix protein and the BM2 proton channel. Expression of the BM1 and the BM2 polypeptides is regulated in part by a pentanucleotide motif translational slippage site that lies at the junction between the BM1 and BM2 ORFs. The pentanucleotide motif, TAATG, contains both a TAA stop codon for termination of M1 translation and an ATG start codon for initiation of M2 in an alternate −1 reading frame. This pentanucleotide motif and flanking sequences have been shown to be important for the regulation of expression of the M1 protein.

The wild-type influenza B segment 7 showing the BM1 and BM2 coding sequences and the pentanucleotide motif in bold underlining are provided below in Table 6.

TABLE 6

Wild-type BM1 and BM2 coding sequence
(SEQ ID NO: 12) influenza
B/Lee/40 Segment 7.

AGCAGAAGCACGCACTTTCTTAAAATGTCGCTGTT
TGGAGACACAATTGCCTACCTGCTTTCACTAATAG
AAGATGGAGAAGGCAAAGCAGAACTAGCTGAAAAA
TTACACTGTTGGTTCGGTGGGAAAGAATTTGACCT
AGATTCTGCTTTGGAATGGATAAAAAACAAAAGGT
GCCTAACTGATATACAAAAAGCACTAATTGGTGCC
TCTATATGCTTTTTAAAACCCAAAGACCAAGAAAG
AAAAAGGAGATTCATCACAGAGCCCCTGTCAGGAA
TGGGAACAACAGCAACAAAGAAGAAAGGCCTAATT
CTAGCTGAGAGAAAAATGAGAAGATGTGTAAGCTT
TCATGAAGCATTTGAAATAGCAGAAGGCCACGAAA
GCTCAGCATTACTATATTGTCTTATGGTCATGTAC
CTAAACCCTGAAAACTATTCAATGCAAGTAAAACT
AGGAACGCTCTGTGCTTTATGCGAGAAACAAGCAT
CGCACTCGCATAGAGCCCATAGCAGAGCAGCAAGG
TCTTCGGTACCTGGAGTAAGACGAGAAATGCAGAT
GGTTTCAGCTATGAACACAGCAAAGACAATGAATG
GAATGGGAAAGGGAGAAGACGTCCAAAAACTAGCA
GAAGAGCTGCAAAACAACATTGGAGTGTTGAGATC
TCTAGGAGCAAGTCAAAAGAATGGAGAAGGAATTG
CCAAAGATGTAATGGAAGTGCTAAAACAGAGCTCT
ATGGGAAATTCAGCTCTTGTGAGGAAATACTTA
ATGCTCGAACCACTTCAGATTCTTTCAATTTGTTC
TTTCATTTTATCAGCTCTCCATTTCATGGCTTGGA
CAATAGGGCATTTGAATCAAATAAGAAGAGGGGTA
AACCTGAAAATACAAATAAGGAATCCAAATAAGGA
GGCAATAAACAGAGAGGTGTCAATTCTGAGACACA
ATTACCAAAAGGAAATCCAAGCCAAAGAAACAATG
AAGAAAATACTCTCTGACAACATGGAAGTATTGGG
TGACCACATAGTAGTTGAAGGGCTTTCAACTGATG
AGATAATAAAAATGGGTGAAACAGTTTTGGAGGTG
GAAGAATTGCAATGAGCCCAATTTTCACTGTATTT
CTTACTATGCATTTAAGCAAATTGTAATCAATGTC
AGTGAATAAAACTGGAAAAAGTGCGTTGTTTCTAC
T

IV. Cell-Based Virus Production System

A. Producing "first generation" mutant viruses

Mutant virus, such as those carrying mutant M2 nucleic acid, can be generated by plasmid-based reverse genetics as described by Neumann et al., Generation of influenza A viruses entirely from clone cDNAs, Proc. Natl. Acad. Sci. USA 96:9345-9350 (1999), herein incorporated by reference in its entirety. Mutant virus, such as those carrying mutant BM2 nucleic acid, can be generated by similar means. Briefly, eukaryotic host cells are transfected with one or more plasmids encoding the eight viral RNAs. Each viral RNA sequence is flanked by an RNA polymerase I promoter and an RNA polymerase I terminator. Notably, the viral RNA encoding the M2 protein includes the mutant M2 nucleic acid sequence. The host cell is additionally transfected with one or more expression plasmids encoding the viral proteins (e.g., polymerases, nucleoproteins and structural proteins), including a wild-type M2 protein. Transfection of the host cell with the viral RNA plasmids results in the synthesis of all eight influenza viral RNAs, one of which harbors the mutant M2 sequence. The co-transfected viral polymerases and nucleoproteins assemble the viral RNAs into functional vRNPs that are replicated and transcribed, ultimately forming infectious influenza virus having a mutant M2 nucleic acid sequence, yet having a functional M2 polypeptide incorporated into the viral lipid envelope.

Alternative methods of producing a "first generation" mutant virus include a ribonucleoprotein (RNP) transfection system that allows the replacement of influenza virus genes with in vitro generated recombinant RNA molecules, as described by Enami and Palese, High-efficiency formation of influenza virus transfectants, J. Virol. 65(5):2711-2713, which is incorporated herein by reference.

The viral RNA is synthesized in vitro and the RNA transcripts are coated with viral nucleoprotein (NP) and polymerise proteins that act as biologically active RNPs in the transfected cell as demonstrated by Luytjes et al., Amplification, expression, and packaging of a foreign gene by influenza virus, Cell 59:1107-1113, which is incorporated herein by reference.

The RNP transfection method can be divided into four steps: 1) Preparation of RNA: plasmid DNA coding for an influenza virus segment is transcribed into negative-sense RNA in an in vitro transcription reaction; 2) Encapsidation of the RNA: the transcribed RNA is then mixed with gradient purified NP and polymerase proteins isolated from disrupted influenza virus to form a biologically active RNP complex; 3) Transfection and rescue of the encapsidated RNA: the artificial ribonucleocapsid is transfected to the cells previously infected with a helper influenza virus that contains a different gene from the one being rescued; the helper virus will amplify the transfected RNA; 4) Selection of transfected gene: because both the helper virus and the transfectant containing the rescued gene are in the culture supernatant, an appropriate selection system using antibodies is necessary to isolate the virus bearing the transfected gene.

The selection system allows for the generation of novel transfectant influenza viruses with specific biological and molecular characteristics. Antibody selection against a target surface protein can then be used for positive or negative selection.

For example, a transfectant or mutant virus that contains an M2 gene that does not express an M2 protein can be grown in a suitable mammalian cell line that has been modified to stably express the wild-type functional M2 protein. To prevent or inhibit replication of the helper virus expressing the wild-type M2 gene, and therefore the M2e protein at the membrane surface, antibodies against M2e can be used. Such antibodies are commercially available and would inhibit the replication of the helper virus and allow for the transfectant/mutant virus containing the mutant M2 to grow and be enriched in the supernatant. Inhibition of influenza virus replication by M2e antibodies has been described previously in Influenza A virus M2 protein: monoclonal antibody restriction of virus growth and detection of M2 in virions, J Virol 62:2762-2772 (1988) and Treanor et al, Passively transferred monoclonal antibody to the M2 protein inhibits influenza A virus replication in mice, J. Virol. 64:1375-1377 (1990).

Additionally or alternatively, the same antibodies can be used to 'capture' the helper virus and allow for the enrichment of the transfectant. For example, the antibodies can be used to coat the bottom of a tissue culture dish or can be used in a column matrix to allow for enrichment for the transfectant in the supernatant or eluate.

The transfectant virus can be grown in M2 expressing cells in multi-well plates by limit dilution and then be identified and cloned, for example, by creating replica plates. For example, one-half of an aliquot of a given well of the multi-well plate containing the grown virus can be used to infect MDCK cells and the other half to infect MDCK cells that express M2 protein. Both the transfectant virus and helper virus will grow in MDCK cells that express M2 protein. However, only helper virus will grow in standard MDCK cells allowing for identifying the well in the multi-well plate that contains the transfectant. The transfectant virus can be further plaque purified in the cells that express M2 protein.

B. Propagating viral mutants

In some embodiments, viral mutants described herein are maintained and passaged in host cells. By way of example, but not by way of limitation, exemplary host cells appropriate for growth of influenza viral mutants, such as influenza A viral mutants include any number of eukaryotic cells, including, but not limited to Madin-Darby canine kidney (MOCK) cells, simian cells such as African green monkey cells (e.g., Vero cells), CV-1 cells and rhesus monkey kidney cells (e.g., LLcomk.2 cells), bovine cells (e.g., MDBK cells), swine cells, ferret cells (e.g., mink lung cells) BK-1 cells, rodent cells (e.g., Chinese Hamster Ovary cells), human cells, e.g., embryonic human retinal cells (e.g., PER-C6®), 293T human embryonic kidney cells and avian cells including embryonic fibroblasts.

Additionally or alternatively, in some embodiments, the eukaryotic host cell is modified to enhance viral production, e.g., by enhancing viral infection of the host cell and/or by enhancing viral growth rate. For example, in some embodiments, the host cell is modified to express, or to have increased expression, of 2,6-linked sialic acid on the cell surface, allowing for more efficient and effective infection of these cells by mutant or wild-type influenza A viruses. See e.g., U.S. Patent Publication No. 2010-0021499, and U.S. Pat. No. 7,176,021, herein incorporated by reference in their entirety. Thus, in some illustrative embodiments, Chinese Hamster Ovary Cells (CHO cells) and/or Vero cells modified to express at least one copy of a 2,6-sialyltransferase gene (ST6GAL 1) are used. By way of example, but not by way of limitation, the *Homo sapiens* ST6 beta-galatosamide alpha-2,6-sialyltransferase gene sequence denoted by the accession number BC040009.1, is one example of a ST6Ga1 gene that can be integrated into and expressed by a CHO cell. One or more copies of a polynucleotide that encodes a functional ST6Gal I gene product can be engineered into a cell. That is, cells which have been stably transformed to express 1, 2, 3, 4, 5, 6, 7, 8, 9, 10, 11, 12, or more than 12 copies of a ST6Gal I gene may be used. A single expression cassette may include one or more copies of the ST6Gal I gene to be expressed, which is operably linked to regulatory elements, such as promoters, enhancers, and terminator and polyadenylation signal sequences, to facilitate the expression of the ST6Gal I gene or its copies. Alternatively, a single expression cassette may be engineered to express one copy of an ST6Gal I gene, and multiple expression cassettes integrated into a host cell genome. Accordingly, in some embodiments, at least one ST6Gal I gene is incorporated into the genome of a host cell, such that the cell expresses the ST6Ga1 I gene and its enzymatic protein product. Depending on the copy number, a single host cell may express many functional ST6Ga1 I gene proteins.

Suitable vectors for cloning, transfecting and producing stable, modified cell lines are well known in the art. One non-limiting example includes the pcDNA3.1 vectors (Invitrogen).

Additionally or alternatively, in some embodiments, the eukaryotic host cell is modified to produce a wild-type version of a mutant viral gene, thereby providing the gene to the virus in trans. For example, a viral strain harboring a mutant M2 protein may exhibit an enhanced growth rate (e.g., greater viral production) when passaged in host cells producing the wild-type M2 protein. In some embodiments, the a viral strain harboring a mutant M2 protein may not grow or replicate in a cell which does not express a wild-type M2 gene. In addition, such host cells may slow or prevent viral reversion to a functional M2 sequence, because, for example, there is no selective pressure for reversion in such a host.

Methods for producing both expression vectors and modified host cells are well known in the art. For example, an M2 expression vector can be made by positioning the M2 nucleic acid sequence (M2 ORF sequence; this is "wild-type" M2's start codon to stop codon (Table 7)) below in a eukaryotic expression vector. Similar methods can be employed for BM2, the sequence of which is provided below in Table 7.

TABLE 7

| Wild-type M2 nucleic acid sequence (SEQ ID NO: 13) |
|---|
| ATGAGTCTTCTAACCGAGGTCGAAACGCCTATCAG<br>AAACGAATGGGGGTGCAGATGCAACGGTTCAAGTG<br>ATCCTCTCACTATTGCCGCAAATATCATTGGGATC<br>TTGCACTTGACATTGTGGATTCTTGATCGTCTTTT<br>TTTCAAATGCATTTACCGTCGCTTTAAATACGGAC<br>TGAAAGGAGGGCCTTCTACGGAAGGAGTGCCAAAG<br>TCTATGAGGGAAGAATATCGAAAGGAACAGCAGAG<br>TGCTGTGGATGCTGACGATGGTCATTTTGTCAGCA<br>TAGAGCTGGAGTAA |

TABLE 8

| Wild-type BM2 nucleic acid sequence (SEQ ID NO: 14) |
|---|
| ATGCTCGAACCACTTCAGATTCTTTCAATTTGTTC<br>TTTCATTTTATCAGCTCTCCATTTCATGGCTTGGA<br>CAATAGGGCATTTGAATCAAATAAGAAGAGGGGTA<br>AACcTGAAAATACAAATAAGGAATCCAAATAAGGA<br>GGCA<br>ATAAACAGAGAGGTGTCAATTCTGAGACACAATTA<br>CCAAAAGGAAATCCAAGCCAAAGAAACAATGAAGA<br>AAATACTCTCTGACAACATGGAAGTATTGGGTGAC<br>CACATAGTAGTTGAAGGGCTTTCAACTGATGAGAT<br>AATAAAAATGGGTGAAACAGTTTTGGAGGTGGAAG<br>AATTGCAATGAGCCCAATTTTCACTGTATTTCTTA<br>CTATGCATTTAAGCAAATTGTAATCAATGTCAGTG<br>AATAAAACTGGAAAAAGTGCGTTGTTTCTACT |

Host cells (e.g., MDCK cells) can then be transfected by methods known in the art, PGP-37,DNA e.g., using commercially available reagents and kits, such as TransIT® LT1 (Minis Bio, Madison, WI). By way of example, but not by way of limitation, cells can be selected and tested for M2 expression by cotransfection with a detectable marker or a selectable marker (e.g., hygromycin-resistance) and/or by screening, for example, with indirect immunostaining using an M2 antibody. M2 expression can be determined by indirect immunostaining, flow cytometry or ELISA.

By way of example, but not by way of limitation, 293T human embryonic kidney cells and Madin-Darby canine kidney (MOCK) cells were maintained in Dulbecco's modified Eagle's medium supplemented with 10% fetal calf serum and in minimal essential medium (MEM) containing 5% newborn calf serum, respectively. All cells were maintained at 37° C. in 5% $CO_2$. Hygromycin-resistant MDCK cells stably expressing M2 protein from A/Puerto Rico/8/34 (H1N1) were established by cotransfection with plasmid pRHyg, containing the hygromycin resistance gene, and plasmid pCAGGS/M2, expressing the full-length M2 protein, at a ratio of 1:1. The stable MDCK cell clone (M2CK) expressing M2 was selected in medium containing 0.15 mg/mL of hygromycin (Roche, Mannheim, Germany) by screening with indirect immunostaining using an anti-M2 (14C2) monoclonal antibody (Iwatsuki et al., JVI, 2006, vol. 80, No. 1, p.5233-5240). The M2CK cells were cultured in MEM supplemented with 10% fetal calf serum and 0.15 mg/mL of hygromycin. In M2CK cells, the expression levels and localization of M2 were similar to those in virus-infected cells (data not shown). BM2-expressing BM2CK cells can be made in a similar fashion, and M2- or BM2-expressing Vero cells can be made in a similar fashion.

In some embodiments, cells and viral mutants are cultured and propagated by methods well known in the art. By way of example, but not by way of limitation, in some embodiments, host cells are grown in the presence of MEM supplemented with 10% fetal calf serum. Cells expressing M2 or BM2 are infected at an MOI of 0.001 by washing with PBS followed by adsorbing virus at 37° C. In some embodiments, viral growth media containing trypsin/TPCK is added and the cells are incubated for 2-3 days until cytopathic effect is observed.

Along these lines, disposable bioreactor systems have been developed for mammalian cells, with or without virus, whose benefits include faster facility setup and reduced risk of cross-contamination. The cells described herein, for instance, can be cultured in disposable bags such as those from Stedim, Bioeaze bags from SAFC Biosciences, HybridBagTM from Cellexus Biosytems, or single use bioreactors from HyClone or Celltainer from Lonza. Bioreactors can be 1 L, 10 L, 50 L, 250 L, 1000 L size formats. In some embodiments, the cells are maintained in suspension in optimized serum free medium, free of animal products. The system can be a fed-batch system where a culture can be expanded in a single bag from 1 L to 10 L for example, or a perfusion system that allows for the constant supply of nutrients while simultaneously avoiding the accumulation of potentially toxic by-products in the culture medium.

For long term storage, mutant virus can be stored as frozen stocks.

V. Vaccines and method of administration

A. Immunogenic compositions and vaccines

There are various different types of vaccines which can be made from the cell-based virus production system disclosed herein. The present disclosure includes, but is not limited to, the manufacture and production of live attenuated virus vaccines, single replication vaccines, replication defective vaccines, viral vector vaccines, inactivated virus vaccines, whole virus vaccines, split virus vaccines, virosomal virus vaccines, viral surface antigen vaccines and combinations thereof. Thus, there are numerous vaccines capable of producing a protective immune response specific for different influenza viruses where appropriate formulations of any of these vaccine types are capable of producing an immune response, e.g., a systemic immune response. Live attenuated virus vaccines have the advantage of also being able to stimulate local mucosal immunity in the respiratory tract.

In some embodiments, vaccine antigens used in the compositions described herein are "direct" antigens, i.e., they are not administered as DNA, but are the antigens themselves. Such vaccines may include a whole virus or only part of the virus, such as, but not limited to viral polysaccharides, whether they are alone or conjugated to carrier elements, such as carrier proteins, live attenuated whole microorganisms, inactivated microorganisms, recombinant peptides and proteins, glycoproteins, glycolipids, lipopeptides, synthetic peptides, or ruptured microorganisms in the case of vaccines referred to as "split" vaccines.

In some embodiments, a complete virion vaccine is provided. A complete virion vaccine can be concentrated by ultrafiltration and then purified by zonal centrifugation or by chromatography. Typically, the virion is inactivated before or after purification using formalin or beta-propiolactone, for instance.

In some embodiments, a subunit vaccine is provided, which comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide, an anionic detergent such as ammonium deoxycholate; or a nonionic detergent such as that commercialized under the name TRITON X100. The hemagglutinin may also be isolated after treatment of the virions with a protease such as bromelin, then purified by standard methods.

In some embodiments, a split vaccine is provided, which comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

In some embodiments, inactivated influenza virus vaccines are provided. In some embodiments, the inactivated vaccines are made by inactivating the virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

Additionally or alternatively, in some embodiments, live attenuated influenza virus vaccines are provided. Such vaccines can be used for preventing or treating influenza virus infection, according to known method steps.

In some embodiments, attenuation is achieved in a single step by transfer of attenuated genes from an attenuated donor virus to an isolate or reassorted virus according to known methods (see, e.g., Murphy, Infect. Dis. Clin. Pract. 2, 174 (1993)). In some embodiments, a virus is attenuated by mutation of one or more viral nucleic acid sequences, resulting in a mutant virus. For example, in some embodiments, the mutant viral nucleic acid sequence codes for a defective protein product. In some embodiments, the protein product has diminished function or no function. In other embodiments, no protein product is produced from the mutant viral nucleic acid.

The single replication virus described herein can be formulated and administered according to known methods, as an immunogenic composition (e.g., as a vaccine) to induce an immune response in an animal, e.g., an avian and/or a mammal. Methods are well-known in the art for determining whether such attenuated or inactivated vaccines have maintained similar antigenicity to that of the clinical isolate or a high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) or other mutant sequences (e.g., M2) are not present in the attenuated viruses. See, e.g., Robertson et al., Giornale di Igiene e Medicina Preventiva, 29, 4 (1988); Kilbourne, Bull. M2 World Health Org., 41, 643 (1969); and Robertson et al., Biologicals, 20, 213 (1992).

In some embodiments, the vaccine includes a single replication influenza virus that lacks expression of a functional M2 protein. In some embodiments, the mutant virus replicates well in cells expressing M2 proteins, but in the corresponding wild-type cells, expresses viral proteins without generating infectious progeny virions.

Pharmaceutical compositions of the present technology, suitable for intranasal administration, intradermal administration, inoculation, or for parenteral or oral administration, comprise attenuated or inactivated influenza viruses, and may optionally further comprise sterile aqueous or non-aqueous solutions, suspensions, and emulsions. The compositions can further comprise auxiliary agents or excipients, as known in the art. See, e.g., Berkow et al., The Merck Manual, 15th edition, Merck and Co., Rahway, N.J. (1987); Goodman et al., eds., Goodman and Gilman's The Pharmacological Basis of Therapeutics, Eighth Edition, Pergamon Press, Inc., Elmsford, N.Y. (1990); Avery's Drug Treatment: Principles and Practice of Clinical Pharmacology and Therapeutics, Third Edition, ADIS Press, LTD., Williams and Wilkins, Baltimore, Md. (1987); and Katzung, ed., Basic and Clinical Pharmacology, Fifth Edition, Appleton and Lange, Norwalk, Conn. (1992).

In some embodiments, liquid preparations for intranasal delivery may take the form of solutions or suspensions and may contain conventional excipients such as tonicity adjusting agents, for example, sodium chloride, dextrose or mannitol; preservatives, for example benzalkonium chloride, thiomersal, phenylethyl alcohol; and other formulating agents such as suspending, buffering, stabilising and/or dispersing agents.

In some embodiments, preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants (substances that augment a specific immune response) can be used. Normally, the adjuvant and the composition are mixed prior to presentation to the immune system, or presented separately, but into the same site of the organism being immunized.

In some embodiments, the present disclosure provides a multivalent immunogenic composition comprising viruses from at least two influenza strains. In some embodiments, the multivalent immunogenic composition comprises: (a) at least one engineered attenuated influenza A M2-deficient recombinant virus, wherein the engineered influenza A viruses comprise a mutant M2 gene comprising SEQ ID NO: 1, SEQ ID NO: 2, or SEQ ID NO: 3; and (b) at least one engineered attenuated influenza BM2-deficient recombinant virus, wherein the engineered influenza B virus comprises a mutant BM2 gene comprising SEQ ID NO: 6, SEQ ID NO: 7, SEQ ID NO: 8, SEQ ID NO: 9, SEQ ID NO: 10, or SEQ ID NO: 11.

In some embodiments, the influenza A viruses are chosen from the group of H1N1 and H3N2 subtypes, and the influenza B viruses are chosen from the group of B/Yamagata and B/Victoria lineages.

In some embodiments, the present disclosure provides a quadrivalent immunogenic composition comprising: two M2-deficient influenza A M2SR viruses: A/California/07/2009 (H1N1) and A/Brisbane/10/2007 (H3N2), both of which comprise an M2SR-1 mutant comprising SEQ ID NO: 1; and two BM2-deficient influenza B BM2SR viruses: B/Brisbane/60/2008 (Victoria) and B/Wisconsin/01/2010 (Yamagata) both of which comprise a BM2SR-0 mutant comprising SEQ ID NO: 11. In some embodiments, this immunogenic composition is formulated as a quadrivalent influenza vaccine.

In some embodiments, the present disclosure provides a method of stimulating an immune response against influenza A and influenza B, comprising administering to a subject in need thereof a multivalent immunogenic composition comprising from at least one influenza A strain and at least one influenza B strain. In some embodiments, the multivalent immunogenic composition comprises: (a) at least one engineered attenuated influenza A M2-deficient recombinant virus, wherein the engineered influenza A viruses comprise a mutant M2 gene comprising SEQ ID NO: 1, SEQ ID NO: 2, or SEQ ID NO: 3; and (b) at least one engineered attenuated influenza BM2-deficient recombinant virus, wherein the engineered influenza B virus comprises a mutant BM2 gene comprising SEQ ID NO: 6, SEQ ID NO: 7, SEQ ID NO: 8, SEQ ID NO: 9, SEQ ID NO: 10, or SEQ ID NO: 11.

In some embodiments, the influenza A viruses are chosen from the group of H1N1 and H3N2 subtypes, and the influenza B viruses are chosen from the group of B/Yamagata and B/Victoria lineages.

In some embodiments, the present disclosure provides a method of stimulating an immune response against influenza A and influenza B, comprising administering to a subject in need thereof an immunogenic composition comprising: two M2-deficient influenza A M2SR viruses: A/California/07/

2009 (H1N1) comprising an M2SR-1 mutant comprising SEQ ID NO: 1 and A/Brisbane/10/2007 (H3N2) comprising an M2SR-1 mutant comprising SEQ ID NO: 1; and two BM2-deficient influenza B BM2SR viruses: B/Brisbane/60/2008 (Victoria) comprising a BM2SR-0 mutant comprising SEQ ID NO: 11 and B/Wisconsin/01/2010 (Yamagata) comprising a BM2SR-0 mutant comprising SEQ ID NO: 11. In some embodiments, this immunogenic composition is formulated as a quadrivalent influenza vaccine.

In some embodiments, the immunogenic composition formulated as a quadrivalent influenza vaccine as described herein exhibits attenuated virulence. For example, in some embodiments, mice infected with the quadrivalent vaccine have an increased average post-infection lifespan after influenza A challenge compared to mice infected with influenza B monovalent vaccines alone. In some embodiments, mice infected with the quadrivalent vaccine have an increased average post-infection lifespan following influenza B challenge compared to mice infected with influenza A monovalent vaccines alone.

A pharmaceutical composition according to the present invention may further or additionally comprise at least one chemotherapeutic compound, e.g., for gene therapy, an immunosuppressant, an anti-inflammatory agent or an immunostimulatory agent, or anti-viral agents including, but not limited to, gamma globulin, amantadine, guanidine, hydroxybenzimidazole, interferon-$\alpha$, interferon-$\beta$, interferon-$\gamma$, tumor necrosis factor-$\alpha$, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition of the invention is administered.

B. Administration

An immunogenic composition (e.g., vaccine) as disclosed herein may be administered via any of the routes conventionally used or recommended for vaccines: parenteral route, mucosal route, and may be in various forms: injectable or sprayable liquid, formulation which has been freeze-dried or dried by atomization or air-dried, etc. Vaccines may be administered by means of a syringe or by means of a needle-free injector for intramuscular, subcutaneous or intradermal injection. Vaccines may also be administered by means of a nebulizer capable of delivering a dry powder or a liquid spray to the mucous membranes, whether they are nasal, pulmonary, vaginal or rectal.

A vaccine as disclosed herein may confer resistance to one or more influenza strains by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain.

The present invention thus includes methods for preventing or attenuating a disease or disorder, e.g., infection by at least one influenza virus strain. As used herein, a vaccine is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described. For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. In some embodiments, an immunogenic composition as disclosed herein is by intramuscular or subcutaneous application.

In some embodiments, a regimen for preventing, suppressing, or treating an influenza virus related pathology comprises administration of an effective amount of a vaccine composition as described herein, administered as a single treatment, or repeated as enhancing or booster dosages, over a period up to and including between one week and about 24 months, or any range or value therein. In some embodiments, an influenza vaccine as disclosed herein is administered annually.

According to the present technology, an "effective amount" of a vaccine composition is one that is sufficient to achieve a desired biological effect. It is understood that, in some embodiments, the effective dosage will be dependent upon the age, sex, health, and weight of the recipient, kind of concurrent treatment, if any, frequency of treatment, and the nature of the effect wanted. The ranges of effective doses provided below are not intended to be limiting and represent exemplary dose ranges. Thus, in some embodiments, the dosage will be tailored to the individual subject, as is understood and determinable by one of skill in the art. The dosage of an attenuated virus vaccine for a mammalian (e.g., human) adult can be from about $10^1$-$10^{10}$ plaque forming units (PFU)/kg, or any range or value therein. In some embodiments, the dosage of an attenuated virus vaccine for a mammalian (e.g., human) adult can be from about $10^2$-$10^{10}$ plaque forming units (PFU)/kg, or any range or value therein. In some embodiments, the dosage of an attenuated virus vaccine for a mammalian (e.g., human) adult can be from about $10^3$-$10^{10}$ plaque forming units (PFU)/kg, or any range or value therein. In some embodiments, the dosage of an attenuated virus vaccine for a mammalian (e.g., human) adult can be from about $10^4$-$10^{10}$ plaque forming units (PFU)/kg, or any range or value therein. In some embodiments, the dosage of an attenuated virus vaccine for a mammalian (e.g., human) adult can be from about $10^5$-$10^{10}$ plaque forming units (PFU)/kg, or any range or value therein. In some embodiments, the dosage of an attenuated virus vaccine for a mammalian (e.g., human) adult can be from about $10^6$-$10^{10}$ plaque forming units (PFU)/kg, or any range or value therein. In some embodiments, the dosage of an attenuated virus vaccine for a mammalian (e.g., human) adult can be from about $10^7$-$10^{10}$ plaque forming units (PFU)/kg, or any range or value therein. In some embodiments, the dosage of an attenuated virus vaccine for a mammalian (e.g., human) adult can be from about $10^8$-$10^{10}$ plaque forming units (PFU)/kg, or any range or value therein. In some embodiments, the dosage of an attenuated virus vaccine for a mammalian (e.g., human) adult can be from about $10^9$-$10^{10}$ plaque forming units (PFU)/kg, or any range or value therein. In some embodiments, the dosage of an attenuated virus vaccine for a mammalian (e.g., human) adult can be from about $10^9$-$10^{10}$ plaque forming units (PFU)/kg, or any range or value therein. In some embodiments, the dosage of an attenuated virus vaccine for a mammalian (e.g., human) adult can be greater than $10^{10}$ plaque forming units (PFU)/kg. The dose of inactivated vaccine can range from about 0.1 to 200, e.g., 50 jig of hemagglutinin protein. However, the dosage should be a safe and effective amount as determined by conventional methods, using existing vaccines as a starting point.

C. Intracutaneous delivery

Live flu vaccines are traditionally delivered intranasally to mimic the natural route of infection and promote a similar immune response to that of natural virus infection. As an alternative, disclosed herein are intradermal delivery methods which involve the use of a novel microneedle device to capitalize on the immunological benefits of intradermal delivery. In some embodiments, an attenuated virus (e.g., an M2 and/or BM2 viral mutant) is used in a vaccine composition for intradermal administration. In some embodiments, M2 and BM2 viral mutants, which do not produce infectious progeny virus, are provided in a quadrivalent vaccine. Thus, any potential of reassortment with wild-type circulating influenza viruses is virtually eliminated.

In embodiments disclosed herein, intradermal delivery (intracutaneous) administers vaccine to the skin. In some embodiments, intradermal delivery is performed using a microneedle delivery device. As disclosed herein, intracutaneous delivery has numerous advantages. For example, the immunogenicity of the vaccine is enhanced by triggering the immunological potential of the skin immune system. The vaccine has direct access to the potent antigen-presenting dendritic cells of the skin, i.e., epidermal Langerhans Cells and dermal dendritic cells. Skin cells produce proinflammatory signals which enhance the immune response to antigens introduced through the skin. Further, the skin immune system produces antigen-specific antibody and cellular immune responses. Intradermal delivery allows for vaccine dose sparing, i.e., lower doses of antigen may be effective, in light of the above factors, when delivered intracutaneously.

And, because the vaccine is delivered to the skin through the device's microneedle array, the risk of unintended needle-sticks is reduced, and intracutaneous vaccine delivery via microneedle array is relatively painless compared to intramuscular injections with conventional needle and syringe.

Microneedle devices are known in the art, are known in the art, including, for example, those described in published U.S. patent applications 2012/0109066, 2011/0172645, 2011/0172639, 2011/0172638, 2011/0172637, and 2011/0172609. Microneedle devices may be made, for example, by fabrication from stainless steel sheets (e.g., Trinity Brand Industries, Georgia; SS 304; 50 µm thick) by wet etching. In some embodiments, individual microneedles have a length of between about 500 µm and 1000 µm, e.g., about 750 µm, and a width of between about 100 µm to 500 µm, e.g., about 200 µm. Vaccine can then be applied to the microneedles as a coating. By way of example, but not by way of limitation, a coating solution may include 1% (w/v) carboxymethyl cellulose sodium salt (low viscosity, USP grad; Carbo-Mer, San Diego CA), 0.5% (w/v) Lutrol F-68 NF (BASF, Mt. Olive, NJ) and the antigen (e.g., soluble HA protein at 5 ng/ml; live, attenuated virus such as the M2 and BM2 mutant virus described herein, etc.). To reach a higher vaccine concentration, the coating solution may be evaporated for 5 to 10 minutes at room temperature (~23° C.). Coating may be performed by a dip coating process. The amount of vaccine per row of microneedles can be determined by submerging the microneedles into 200 µl of phosphate-buffered saline (PBS) for 5 minutes and assaying for the antigen by methods known in the art.

In some embodiments, a microneedle device is used that is made mainly of polypropylene and stainless steel first-cut pieces that fit together with simple snap fits and heat seals. In some embodiments, the device is completely self-contained and includes the vaccine, a pump mechanism, an activation mechanism, and a microneedle unit. These components are hidden within a plastic cover. With the device, vaccine infusion is initiated by pressing an actuation button. Pressing the button simultaneously inserts the microneedles into the skin and initiates the pumping mechanism that exerts pressure on the primary drug container. When a spring mechanism exerts sufficient pressure on the vaccine reservoir, vaccine begins to flow through the microneedle array, and into the skin. In some embodiments, the delivery of the vaccine dose is completed within about 2 minutes after actuation of the device. After infusion is complete, the device is gently removed from the skin.

In some embodiments, a method for intracutaneous administration of an immunogenic composition (e.g., quadrivalent vaccine) is provided using a microneedle device. In some embodiments, the microneedle device comprises a puncture mechanism and an immunogenic composition layer comprising a plurality of microneedles capable of puncturing skin and allowing an immunogenic composition to be administered intracutaneously. In some embodiments, the method comprises depressing the puncture mechanism. In some embodiments, the immunogenic composition (e.g., quadrivalent vaccine) comprises a virus comprising a nucleic acid sequence encoding a mutant M2 and BM2 protein that is expressed or a mutant M2 and BM2 protein that is not expressed; wherein the expressed mutant M2 protein comprises, or consists of, the amino acid sequence encoded by SEQ ID NO: 1, SEQ ID NO: 2, or SEQ ID NO: 3, and the BM2 protein comprises, or consists of, the amino acid sequence encoded by SEQ ID NO: 6, SEQ ID NO: 7, SEQ ID NO: 8, SEQ ID NO: 9, SEQ ID NO: 10, or SEQ ID NO: 11. In some embodiments, the microneedle array is initially positioned inside of a device housing, and upon actuation of a lever allows the microneedles to extend through the device bottom and insert into the skin thereby allowing infusion of the vaccine fluid into the skin.

The delivery device described herein may be utilized to deliver any substance that may be desired. In one embodiment, the substance to be delivered is a drug, and the delivery device is a drug delivery device configured to deliver the drug to a subject. As used herein the term "drug" is intended to include any substance delivered to a subject for any therapeutic, preventative or medicinal purpose (e.g., vaccines, pharmaceuticals, nutrients, nutraceuticals, etc.). In one such embodiment, the drug delivery device is a vaccine delivery device configured to deliver a dose of vaccine to a subject. In one embodiment, the delivery device is configured to deliver a flu vaccine. The embodiments discussed herein relate primarily to a device configured to deliver a substance transcutaneously. In some embodiments, the device may be configured to deliver a substance directly to an organ other than the skin.

EXAMPLES

As described above, the present application provides a novel quadrivalent immunogenic composition comprising influenza A and influenza B mutant strains useful in eliciting an immune response in a mammal against influenza A and influenza B. The following examples are presented to illustrate methods of eliciting an immune response with the mutants formulated as multivalent vaccines, and methods of testing the attenuated virulence of the multivalent formulations.

The following examples are provided by way of illustration only and not by way of limitation. Those of skill in the art will readily recognize a variety of non-critical parameters that could be changed or modified to yield essentially the same or similar results. The examples should in no way be construed as limiting the scope of the present technology, as defined by the appended claims.

Example 1: BM2SR Mutants Elicit Antibody Responses Against Influenza B Virus Formulated as Quadrivalent Vaccine An experiment was performed to demonstrate that BM2SR mutant viruses elicit antibody responses when formulated as a quadrivalent vaccine. The following four monovalent vaccines were formulated together: A/California/07/2009 (H1N1) comprising an M2SR-1 mutant comprising SEQ ID NO: 1, A/Brisbane/10/2007 (H3N2) comprising an M2SR-1 mutant comprising SEQ ID NO: 1, B/Brisbane/60/2008 (Victoria) comprising a BM2SR-0 mutant comprising SEQ ID NO: 11, and B/Wisconsin/01/2010 (Yamagata) comprising a BM2SR-0 mutant comprising SEQ ID NO: 11. $1 \times 10^6$ $TCID_{50}$ of each monovalent is mixed together such that each quadrivalent dose is $4 \times 10^6$ $TCID_{50}$ per mouse. The sequence of each of the M2SR-1 and BM2SR-0 mutant constructs is provided in Tables 1 and 5.

Figure 2:
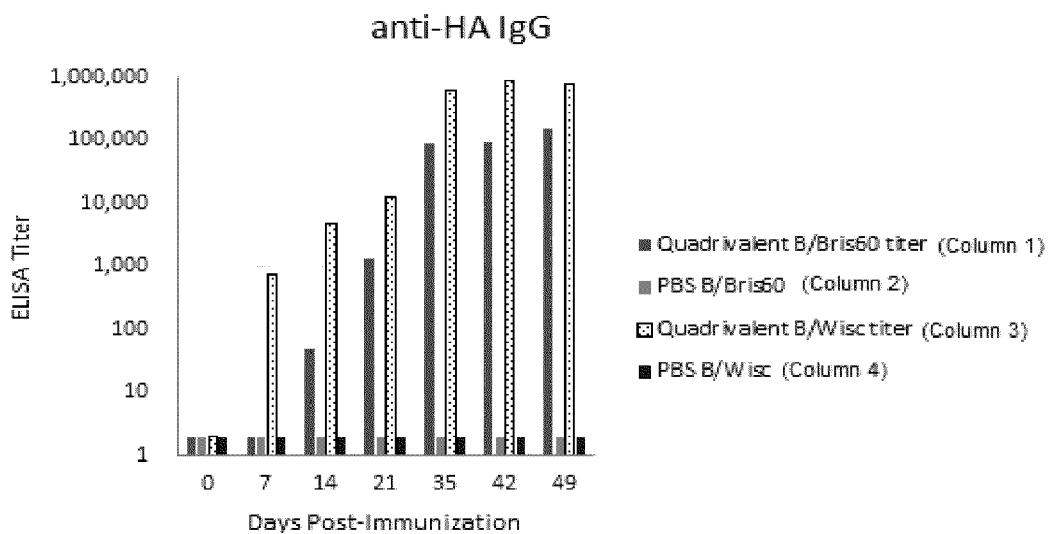
FIG. 2 is a chart showing the anti-HA IgG antibody response elicited by BM2SR viruses in a quadrivalent vaccine formulation.

Six-week-old BALB/c female mice were inoculated intranasally with the quadrivalent formulation at a dose of $4 \times 10^6$ $TCID_{50}$ per mouse. A control group of mice was given PBS. Serum samples were taken on days 7, 14, and 21 after prime inoculation and on days 35, 42 and 49 after the second immunization on day 28. Anti-HA IgG antibody titers from the serum samples were determined by enzyme-linked immunosorbent assay (ELISA) against B/Wisconsin/01/2010 and B/Brisbane/60/2008. The humoral response is shown in FIG. 2, which shows that the quadrivalent M2SR and BM2SR vaccine elevated anti-influenza virus antibodies higher than the control PBS group against both influenza B antigens representing the two influenza B lineages (BBris/60 and B/Wisc/01). Mice boosted by quadrivalent vaccine had higher level of anti-influenza HA antibodies after the second immunization than after the prime dose.

These results demonstrate that each monovalent BM2SR vaccine is capable of eliciting antigen specific responses in a quadrivalent formulation.

Example 2: M2SR and BM2SR Mutants Elicit Antibody Responses Against Influenza A and Influenza B Viruses Formulated in Multivalent Vaccines A. BM2SR mutants elicit antibody responses against influenza B virus formulated in multivalent vaccines An experiment was performed to demonstrate that BM2SR mutant viruses elicit antibody responses when formulated as a monovalent, bivalent, trivalent, or quadrivalent vaccine with the influenza A H1N1 or H3N2 M2SR vaccines. Table A shows how the different formulations of the following four monovalent M2SR and BM2SR vaccines were formulated together: A/California/07/2009 (H1N1) (comprising an M2SR-1 mutant comprising SEQ ID NO: 1, A/Brisbane/10/2007 (H3N2) (comprising an M2SR-1 mutant comprising SEQ ID NO: 1), B/Brisbane/60/2008 (Victoria) (comprising a BM2SR-0 mutant comprising SEQ ID NO: 11), B/Wisconsin/01/2010 (Yamagata) (comprising a BM2SR-0 mutant comprising SEQ ID NO: 11).

TABLE A

Multivalent formulations of M2SR and BM2SR Mouse Grouping (N = 5)

| | | M2SR viruses ($1 \times 10^6$ TCID50/ mouse each) | | | | Total virus titer |
|---|---|---|---|---|---|---|
| | groups | A/ CA07 (H1N1) | A/ Bris10 (H3N2) | B/ WI01 (Yamagata) | B/ Bris60 (Victoria) | (TCID50) per mouse |
| 1 | monovalent CA07 | X | | | | $1 \times 10^6$ |
| 2 | monovalent Bris10 | | X | | | $1 \times 10^6$ |
| 3 | monovalent B/WI01 | | | X | | $1 \times 10^6$ |
| 4 | monovalent B/Bris60 | | | | X | $1 \times 10^6$ |
| 5 | bivalent H1H3 | X | X | | | $2 \times 10^6$ |
| 6 | trivalent H3VY | | X | X | X | $3 \times 10^6$ |
| 7 | trivalent H1VY | X | | X | X | $3 \times 10^6$ |
| 8 | trivalent H1H3V | X | X | | X | $3 \times 10^6$ |
| 9 | trivalent H1H3Y | X | X | X | | $3 \times 10^6$ |
| 10 | Quadrivalent | X | X | X | X | $4 \times 10^6$ |
| 11 | Naive | | | | | none |

X = component is present in formulation

Figure 3A:
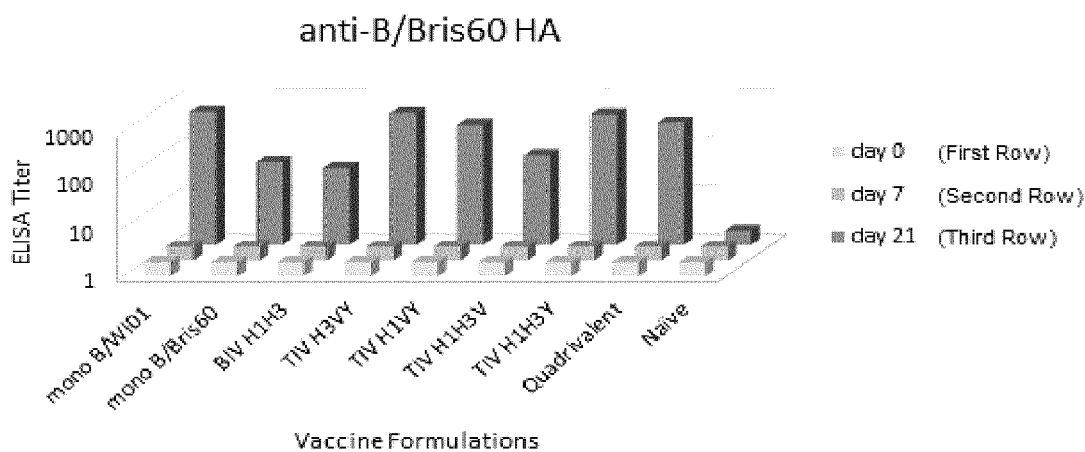
FIGS. 3A-3D are charts showing the anti-HA IgG antibody responses elicited by BM2SR and M2SR viruses in multivalent formulations. Mono/B WI01=monovalent B/WI01 (comprising a BM2SR-0 mutant comprising SEQ ID NO: 11); mono BBris60=monovalent BBris60 (comprising a BM2SR-0 mutant comprising SEQ ID NO: 11); mono CA07=monovalent CA07 (comprising an M2SR-1 mutant comprising SEQ ID NO: 1); mono Bris10=monovalent Bris 10 (comprising an M2SR-1 mutant comprising SEQ ID NO: 1); BIV H1H3=bivalent H1H3 (comprising M2SR-1 mutants comprising SEQ ID NO: 1); TN H3VY=trivalent H3VY (comprising M2SR-1 mutant comprising SEQ ID NO: 1 and BM2SR-0 mutants comprising SEQ ID NO: 11); TN H1VY=trivalent H1VY (comprising M2SR-1 mutants comprising SEQ ID NO: 1, and BM2SR-0 mutant comprising SEQ ID NO: 11); TN H1H3V=trivalent H1H3V (comprising M2SR-1 mutants comprising SEQ ID NO: 1, and BM2SR-0 mutant comprising SEQ ID NO: 11); TIV H1H3Y=trivalent H1H3Y (comprising M2SR-1 mutants comprising SEQ ID NO: 1, and BM2SR-0 mutant comprising SEQ ID NO: 11); Quadrivalent (comprising M2SR-1 mutants comprising SEQ ID NO: 1, and BM2SR-0 mutants comprising SEQ ID NO: 11).
Figure 3B:
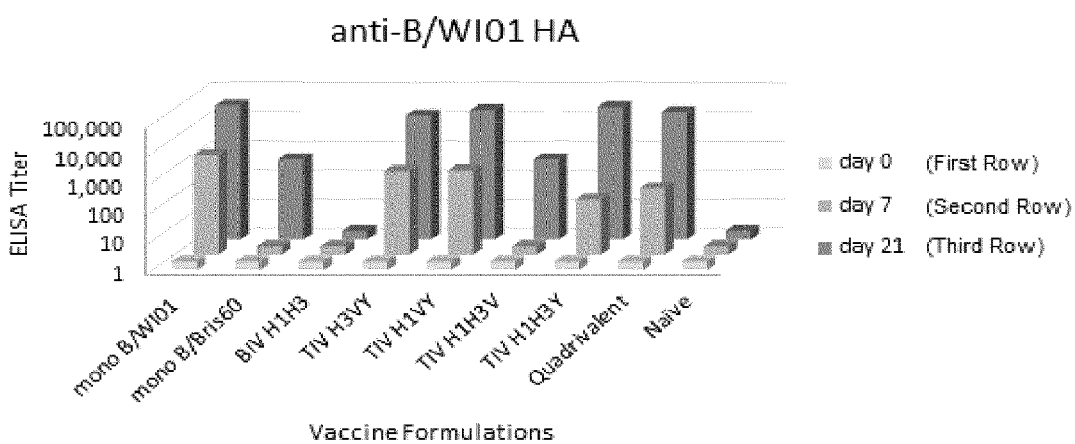

Six-week-old BALB/c female mice were inoculated intranasally with monovalent, bivalent, trivalent, or quadrivalent vaccines at doses shown in Table A. A control group of mice was given PBS. Serum samples were taken on days 7, 14, and 21 after prime inoculation and on days 35, 42 and 49 after the second immunization on day 28. Anti-HA IgG antibody titers from the serum samples were determined by enzyme-linked immunosorbent assay (ELISA) against B/Wisconsin/01/2010 and B/Brisbane/60/2008. The humoral response is shown in FIGS. 3A-3B, which show that both BM2SR vaccine components (Bris60 and WI01) elevated anti-influenza virus antibodies higher than the control PBS group against both influenza B antigens representing the two influenza B lineages in multivalent formulations.

These results demonstrate that there is no interference between the monovalent components when formulated into multivalent vaccines.

B. M2SR mutants elicit antibody responses against influenza A virus formulated in multivalent vaccines An experiment was performed to demonstrate that M2SR mutant viruses elicit antibody responses when formulated as a monovalent, bivalent, trivalent, or quadrivalent vaccine with the influenza B Yamagata or Victoria lineage BM2SR vaccines. Table A shows how the different formulations of the following four monovalent M2SR and BM2SR vaccines were formulated together: A/California/07/2009 (H1N1) (comprising an M2SR-1 mutant comprising SEQ ID NO: 1) A/Brisbane/10/2007 (H3N2) (comprising an M2SR-1 mutant comprising SEQ ID NO: 1), B/Brisbane/60/2008 (Victoria) (comprising a BM2SR-0 mutant comprising SEQ ID NO: 11), B/Wisconsin/01/2010 (Yamagata) (comprising a BM2SR mutant comprising SEQ ID NO: 11).

Figure 3C:
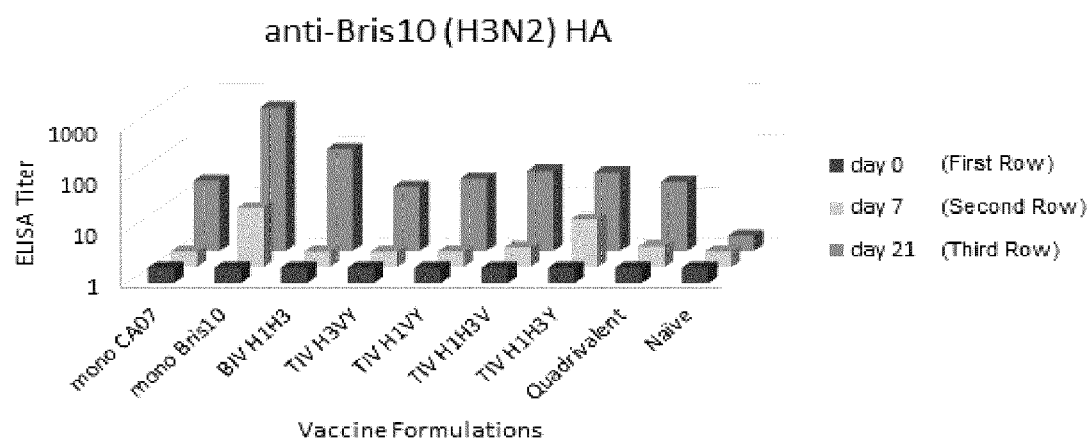
Figure 3D:
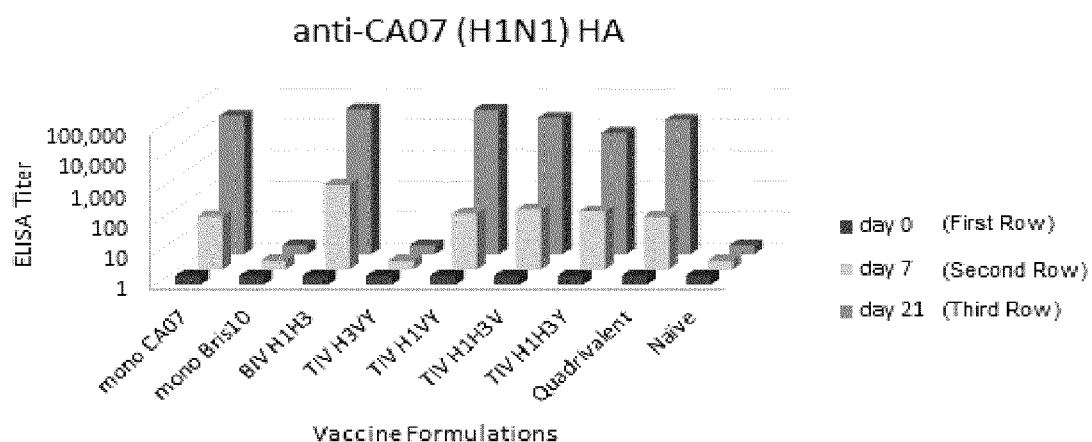

Six-week-old BALB/c female mice were inoculated intranasally with monovalent, bivalent, trivalent, or quadrivalent vaccines at doses shown in Table A. A control group of mice was given PBS. Serum samples were taken on days 7, 14, and 21 after prime inoculation and on days 35, 42, and 49 after the second immunization on day 28. Anti-HA IgG antibody titers from the serum samples were determined by enzyme-linked immunosorbent assay (ELISA) against A/California/07/2009 (H1N1) and A/Brisbane/10/2007 (H3N2). The humoral response is shown in FIGS. 3C-3D, which shows that both influenza A M2SR vaccine components (H1N1 and H3N2) elevated anti-influenza virus antibodies higher than the control PBS group against both influenza A antigens representing the H1N1 and H3N2 subtypes in multivalent formulations.

These results demonstrate that there is no interference between the monovalent components when formulated into multivalent vaccines.

Figure 4A:
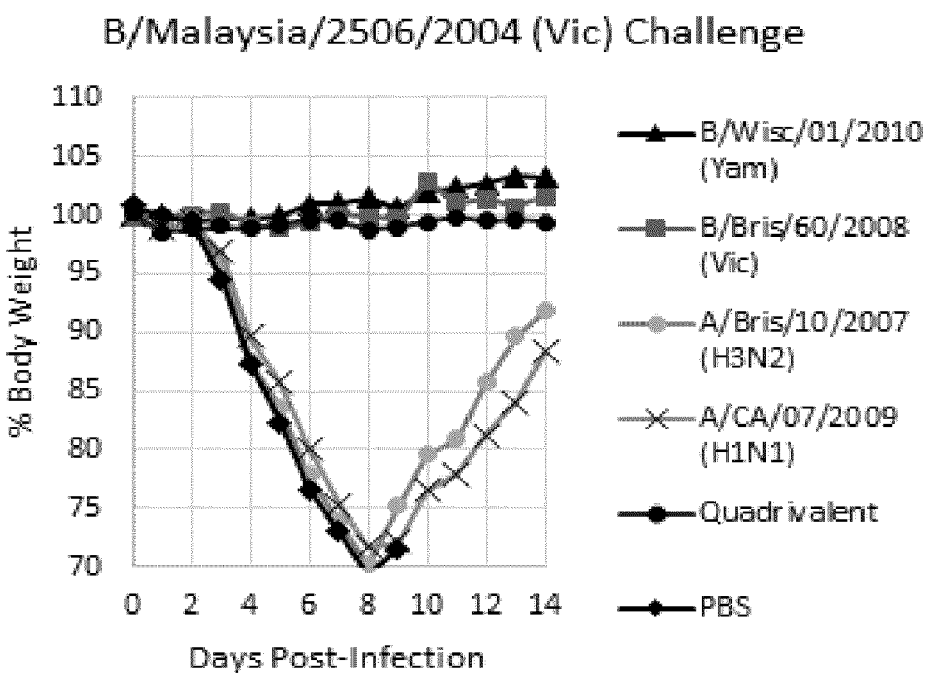
FIG. 4A is a chart showing change in mouse body weight after influenza B challenge, post-inoculation with monovalent BM2SR, monovalent M2SR, and quadrivalent vaccines.
Figure 4B:
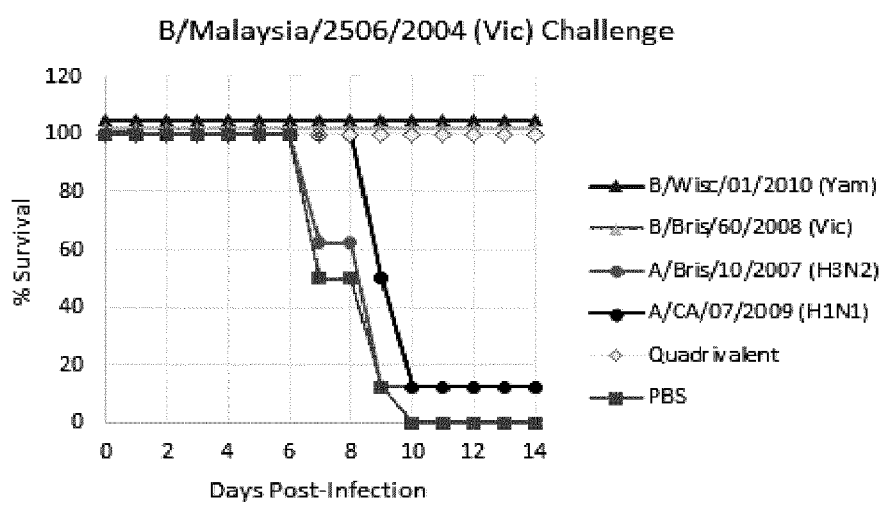
FIG. 4B is a chart showing mouse survival after influenza B challenge, post-inoculation with monovalent BM2SR, monovalent M2SR, and quadrivalent vaccines.
Figure 4C:
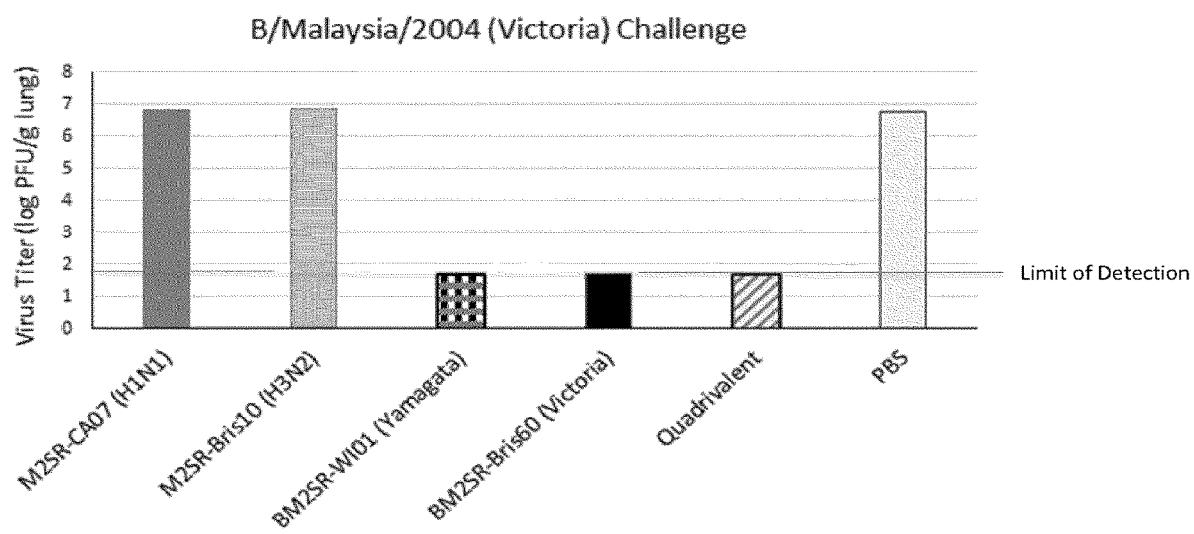
FIG. 4C is a chart showing the virus titers of mice from different vaccination groups at Day 4 post influenza B challenge.

Example 3: BM2SR Mutants Protect Mice from Lethal Influenza B Virus Challenge as Monovalent or Quadrivalent Formulations BALB/c female mice (N=8) were challenged with a lethal dose of B/Malaysia/2506/2004 virus (20 mouse 50% lethal dose (MLD50)) 49 days after the first inoculation (3 weeks after the boost). As shown in FIGS. 4A and 4B, all mice vaccinated with the BM2SR and quadrivalent vaccines survived the challenge and lost no weight. The control mice that were given only PBS, however, lost body weight and did not survive 9 days past the challenge date. On day 4 after the challenge, lungs were obtained and virus titers determined in MDCK cells by plaque assay. As depicted in FIG. 4C, lung virus titers in BM2SR and quadrivalent vaccinated mice were below the limit of detection, whereas nave control PBS mice had high virus titers indicating that the BM2SR and quadrivalent vaccines confer cross-protection and limit the replication of the challenge virus.

Figure 5A:
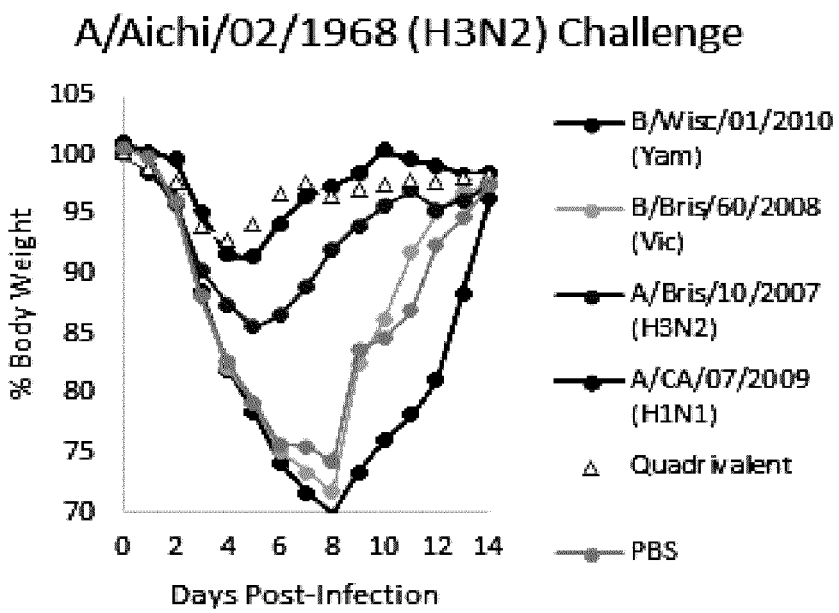
FIG. 5A is a chart showing change in mouse body weight after influenza A challenge, post-inoculation with monovalent BM2SR, monovalent M2SR, and quadrivalent vaccines.
Figure 5B:
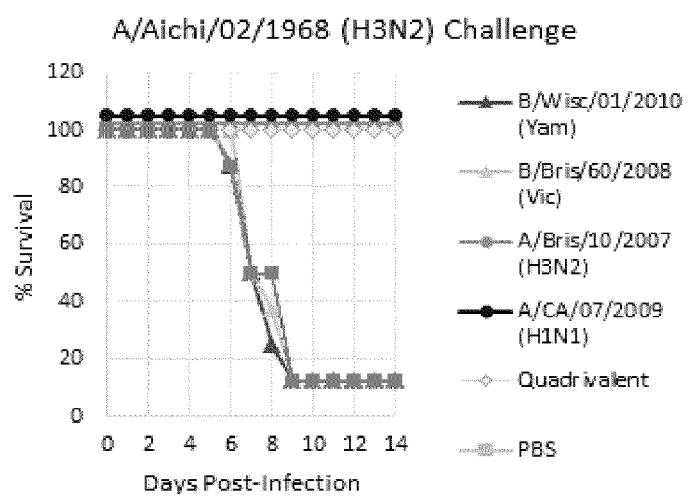
FIG. 5B is a chart showing mouse survival after influenza A challenge, post-inoculation with monovalent BM2SR, monovalent M2SR, and quadrivalent vaccines.
Figure 5C:
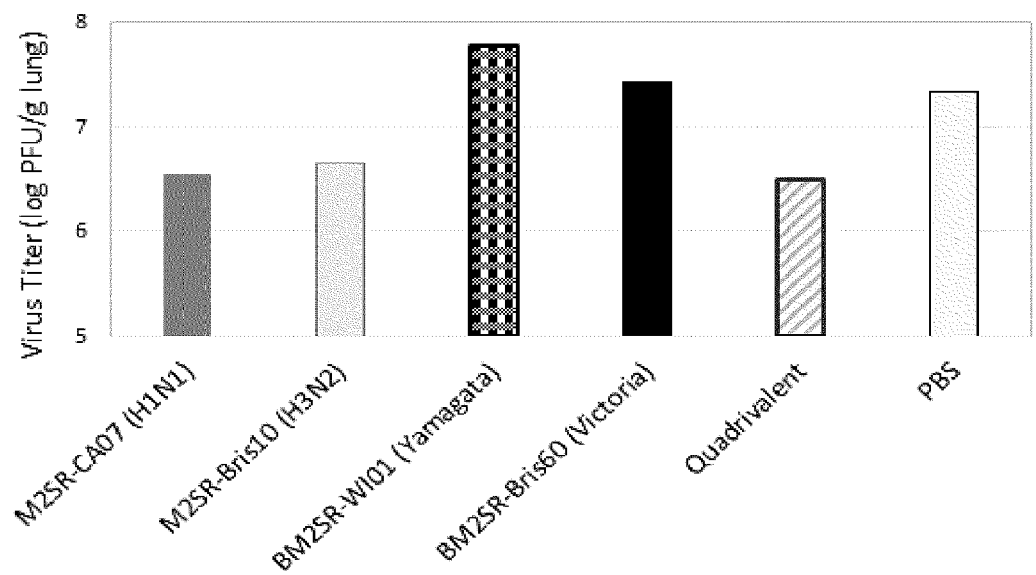
FIG. 5C is a chart showing the virus titers of mice from different vaccination groups at day 4 post influenza A challenge.

Example 4: Quadrivalent M2SR Vaccine Protects Mice from Lethal Influenza a Virus Challenge BALB/c female mice (N=8) were challenged with a lethal dose of A/Aichi/02/1968 (H3N2) virus (40 mouse 50% lethal dose (M.D50)) 49 days after the first inoculation (3 weeks after the boost). As shown in FIGS. 5A and 5B, all mice vaccinated with the monovalent H1N1 or H3N2 M2SR and quadrivalent M2SR vaccines survived the challenge and lost transient weight but fully recovered. The control mice that were given only PBS, however, lost body weight and did not survive 8 days past the challenge date. On day 4 after the challenge, lungs were obtained and virus titers determined in MDCK cells by plaque assay. As depicted in Figure SC, lung virus titers in M2SR monovalents and quadrivalent vaccinated mice were at least a log lower than nave control PBS mice indicating that the M2SR monovalents and quadrivalent M2SR vaccines confer cross-protection and limit the replication of the challenge virus that does not match any vaccine component.

Example 5: BM2SR Mutants Elicit Antibody Responses Against Influenza B Virus Formulated as Quadrivalent Vaccine An experiment to demonstrate that BM2SR mutant viruses elicit antibody responses when formulated as a quadrivalent vaccine was performed. The following four monovalent vaccines were formulated together: an H1N1 influenza A virus comprising an M2SR-1 mutant comprising SEQ ID NO: 1, an H3N2 influenza A virus comprising an M2SR-1 mutant comprising SEQ ID NO: 1, an influenza B virus of Victoria lineage comprising a BM2SR-4 mutant comprising SEQ ID NO: 9, and an influenza B virus of Yamagata lineage comprising a BM2SR-4 mutant comprising SEQ ID NO: 9. $0.2\text{-}1\times10^6$ $TCID_{50}$ of each monovalent were mixed together such that each quadrivalent dose was $3\times10^6$ $TCID_{50}$ per mouse. The sequence of each of the M2SR-1 and BM2SR-4 mutant constructs is provided in Tables 1 and 5.

Six-week-old BALB/c female mice were inoculated intranasally with the quadrivalent formulation at a dose of $3\times10^6$ $TCID_{50}$ per mouse. A control group of mice was given PBS. Serum samples were taken on day 14 after prime inoculation. Anti-HA IgG antibody titers from the serum samples were determined by enzyme-linked immunosorbent assay (ELISA) against influenza antigens (B/Victoria and B/Yamagata lineages). As shown in FIGS. 6A and 6B, the quadrivalent M2SR and BM2SR vaccine elevated anti-influenza virus antibodies higher than the control PBS group against both influenza B antigens representing the two influenza B lineages.

These results demonstrate that each monovalent BM2SR vaccine is capable of eliciting antigen specific responses in a quadrivalent formulation.

Example 6: M2SR and BM2SR Mutants Elicit Antibody Responses Against Influenza a and Influenza B Viruses Formulated in Multivalent Vaccines A. BM2SR mutants elicit antibody responses against influenza B virus formulated in multivalent vaccines An experiment to demonstrate that BM2SR mutant viruses elicit antibody responses when formulated as a monovalent, trivalent, or quadrivalent vaccine with the influenza A H1N1 or H3N2 M2SR vaccines is performed. The following four monovalent M2SR and BM2SR vaccines are formulated together: H1N1 (comprising an M2SR-1 mutant comprising SEQ ID NO: 1, H3N2 (comprising an M2SR-1 mutant comprising SEQ ID NO: 1), B/Victoria-lineage (comprising a BM2SR-4 mutant comprising SEQ ID NO: 9), B/Yamagata (comprising a BM2SR-4 mutant comprising SEQ ID NO: 9).

Six-week-old BALB/c female mice are inoculated intranasally with monovalent, trivalent, or quadrivalent vaccines. A control group of mice was given PBS. Serum samples were taken on day 14 after prime inoculation. Anti-HA IgG antibody titers from the serum samples are determined by enzyme-linked immunosorbent assay (ELISA) against both influenza B antigens. As shown in FIGS. 7C and 7D, both BM2SR vaccine components were higher than the control PBS group against influenza B antigens representing the two influenza B lineages in multivalent formulations.

These results demonstrate that there is no interference between the monovalent components when formulated into multivalent vaccines.

B. M2SR mutants elicit antibody responses against influenza A virus formulated in multivalent vaccines An experiment to demonstrate that M2SR mutant viruses elicit antibody responses when formulated as a monovalent, trivalent, or quadrivalent vaccine with the influenza B Yamagata or Victoria lineage BM2SR vaccines was performed. The following four monovalent M2SR and BM2SR vaccines were formulated together: H1N1 (comprising an M2SR-1 mutant comprising SEQ ID NO: 1), H3N2 (comprising an M2SR-1 mutant comprising SEQ ID NO: 1), B/Victoria-lineage (comprising a BM2SR-4 mutant comprising SEQ ID NO: 9), B/Yamagata (comprising a BM2SR-4 mutant comprising SEQ ID NO: 9).

Six-week-old BALB/c female mice were inoculated intranasally with monovalent, trivalent, or quadrivalent vaccines. A control group of mice was given PBS. Serum samples were taken on day 14 after prime inoculation. Anti-HA IgG antibody titers from the serum samples were determined by enzyme-linked immunosorbent assay (ELISA) against H1N1 and H3N2 influenza A virus. As shown in FIGS. 7A and 7B, both influenza A M2SR vaccine components (H1N1 and H3N2) elevated anti-influenza virus antibodies higher than the control PBS group against both influenza A antigens representing the H1N1 and H3N2 subtypes in multivalent formulations.

These results demonstrate that there is no interference between the monovalent components when formulated into multivalent vaccines.

Figure 8A:
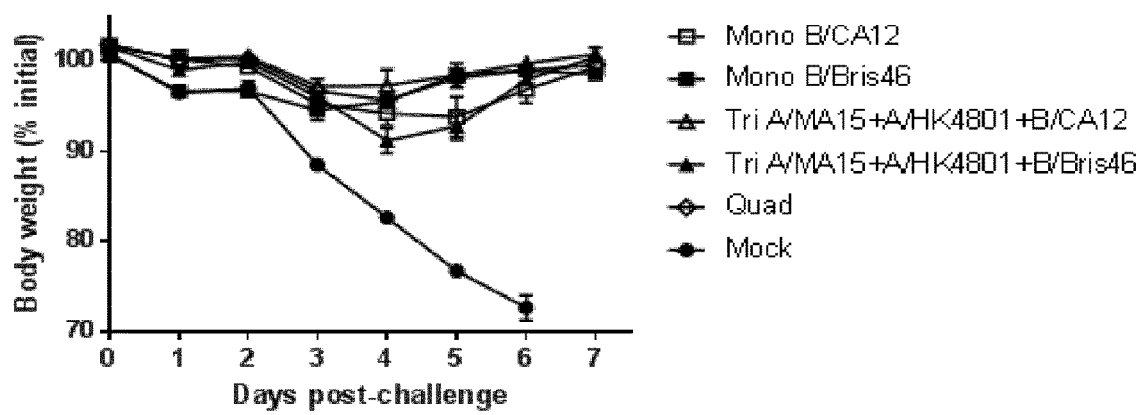
FIGS. 8A-8B are charts showing mouse body weight change and survival, respectively, after a lethal dose influenza B challenge, post-inoculation with monovalent BM2SR, trivalent, and quadrivalent formulations.
Figure 8B:
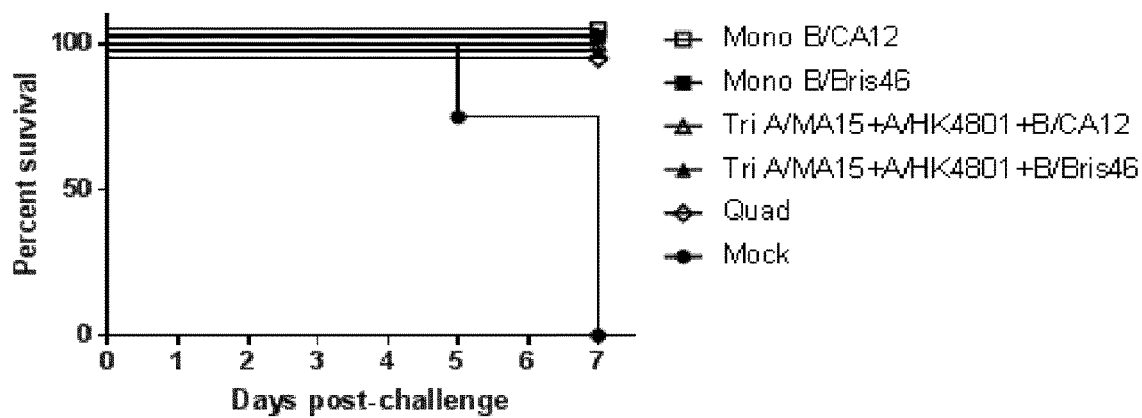

Example 7: BM2SR-4 mutants protect mice from lethal influenza B virus challenge as monovalent, trivalent, or quadrivalent formulations BALB/c female mice (N=4) were challenged with a lethal dose of a heterosubtypic influenza B virus, B/Malaysia/2506/2004 virus (20 mouse 50% lethal dose ($MLD_{50}$)), 22 days after the inoculation. All mice vaccinated with the BM2SR-4 monovalent, trivalent, and quadrivalent vaccines survived the challenge (FIG. 8B) and lost no weight (FIG. 8A). The control mice that were given only PBS, however, lost body weight and did not survive challenge. These results indicate that the monovalent BM2SR-4 vaccines (each one different than challenge virus), trivalent and quadrivalent vaccines confer cross-protection against the challenge virus. These results demonstrate that there is no interference between the monovalent components in multivalent formulations.

Figure 9A:
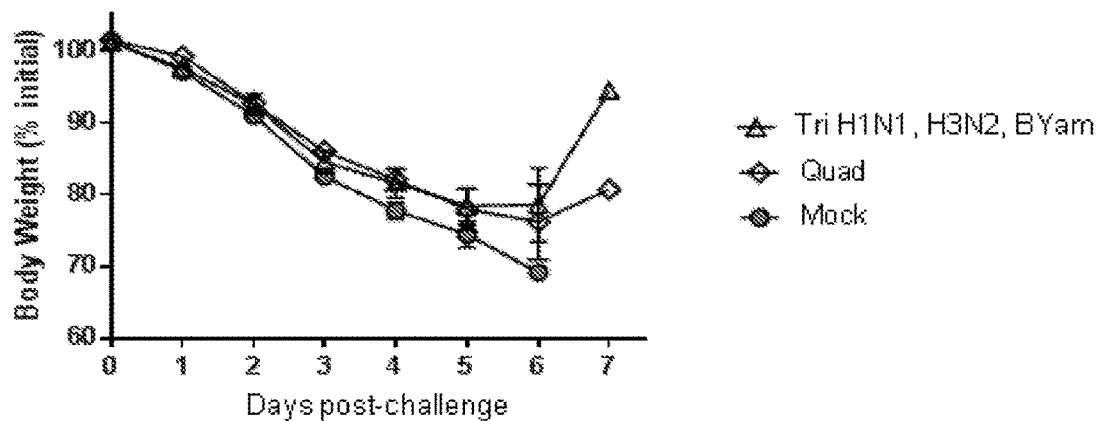
FIGS. 9A-9B are charts showing mouse body weight change and survival, respectively, after a lethal dose influenza A challenge, post-inoculation with trivalent M2SR formulation (comprising H1N1 comprising an M2SR-1 mutant comprising SEQ ID NO: 1), H3N2 (comprising an M2SR-1 mutant comprising SEQ ID NO: 1), and B/Yamagata (comprising a BM2SR-4 mutant comprising SEQ ID NO: 9)) or a quadrivalent M2SR formulation (comprising H1N1 (comprising H1N1 (comprising an M2SR-1 mutant comprising SEQ ID NO: 1), H3N2 (comprising an M2SR-1 mutant comprising SEQ ID NO: 1), B/Victoria lineage (comprising a BM2SR-4 mutant comprising SEQ ID NO: 9, and B/Yamagata (comprising a BM2SR-4 mutant comprising SEQ ID NO: 9)).
Figure 9B:
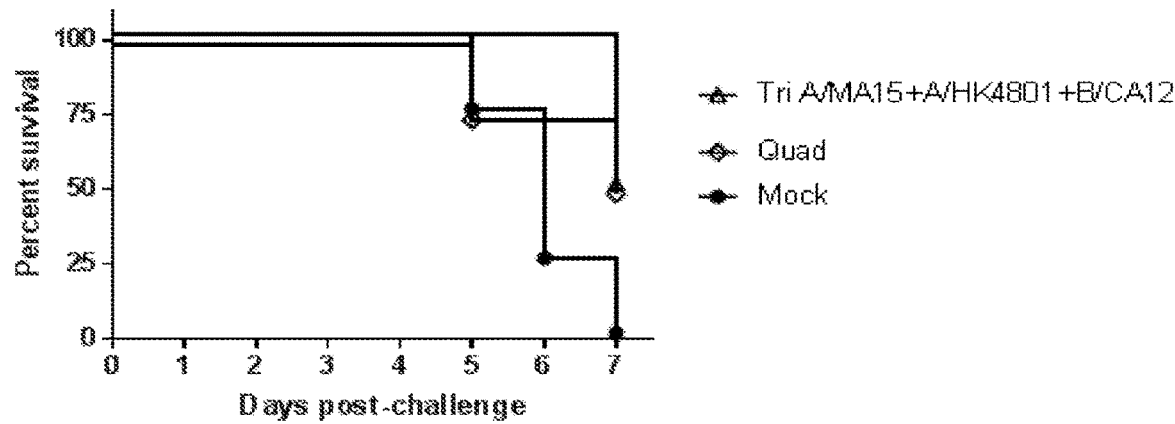
Figure 10:
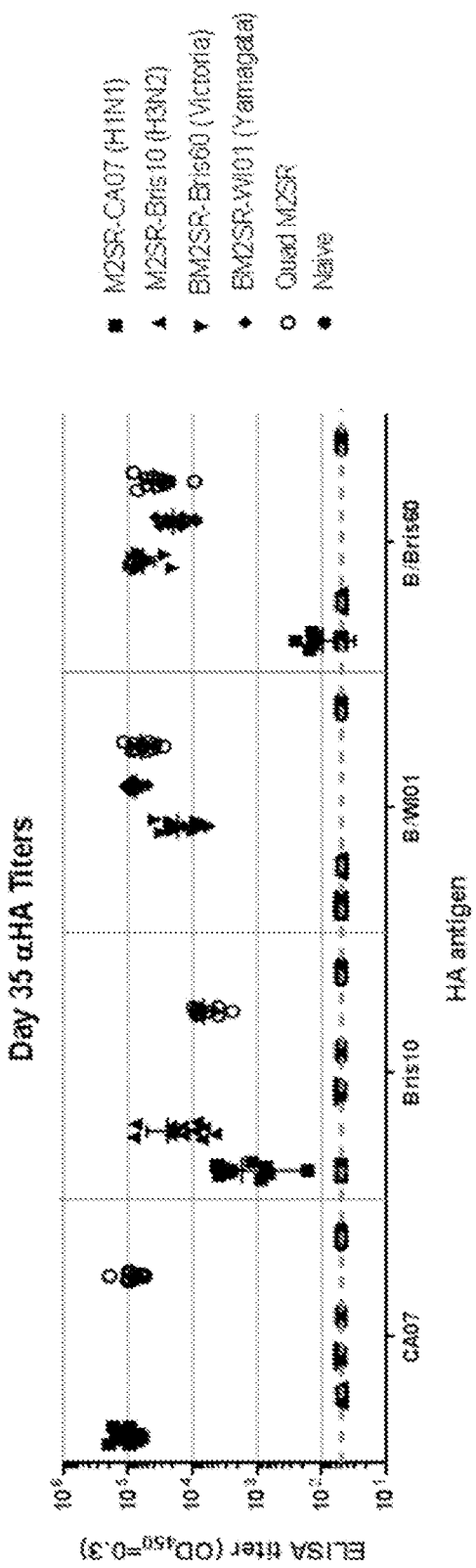
FIG. 10 is a chart showing enzyme-linked immunosorbent assay (ELISA) titers elicited against each component of a quadrivalent vaccine.
Figures 11A, 11B:
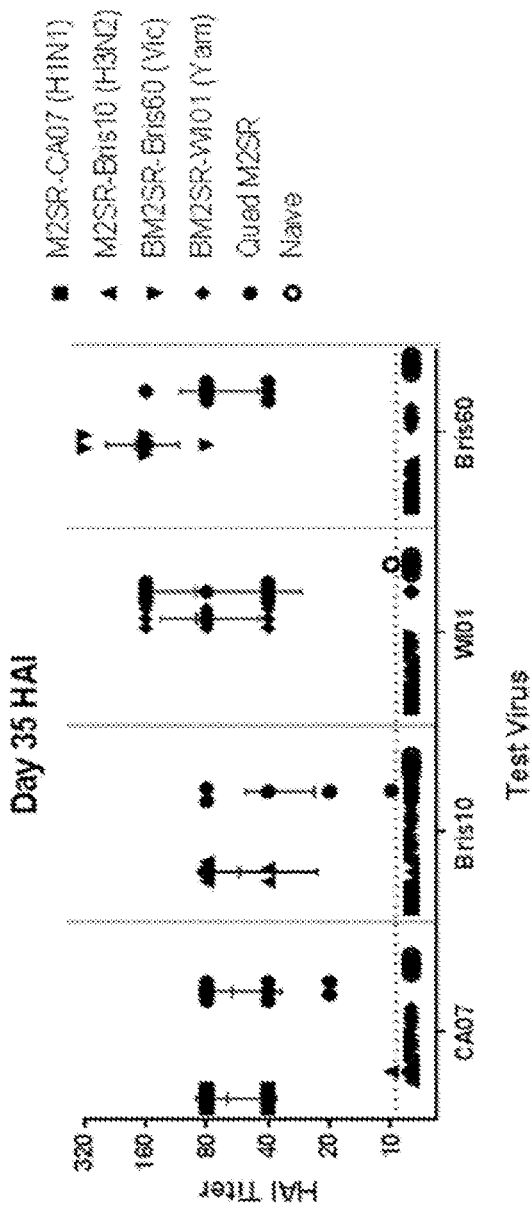
FIG. 11A is a chart showing hemagglutination inhibition (HAI) titers elicited against each component of a quadrivalent vaccine.
FIG. 11B is a table showing HAI titers elicited against each component of a quadrivalent vaccine in pooled sera at day 35 post inoculation.
Figure 12:
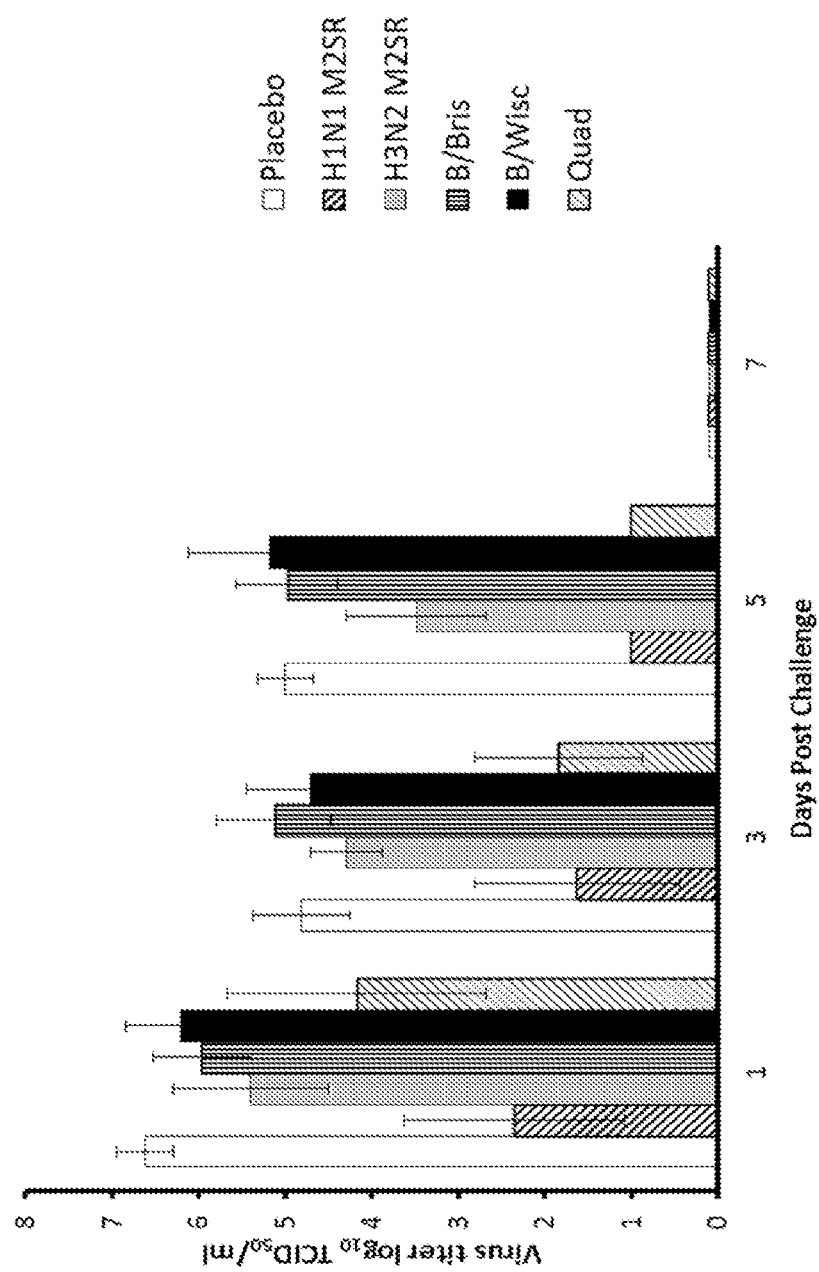
FIG. 12 is a chart showing nasal wash virus titers on days 1, 3, 5, and 7 post influenza A challenge.
Figure 13A:
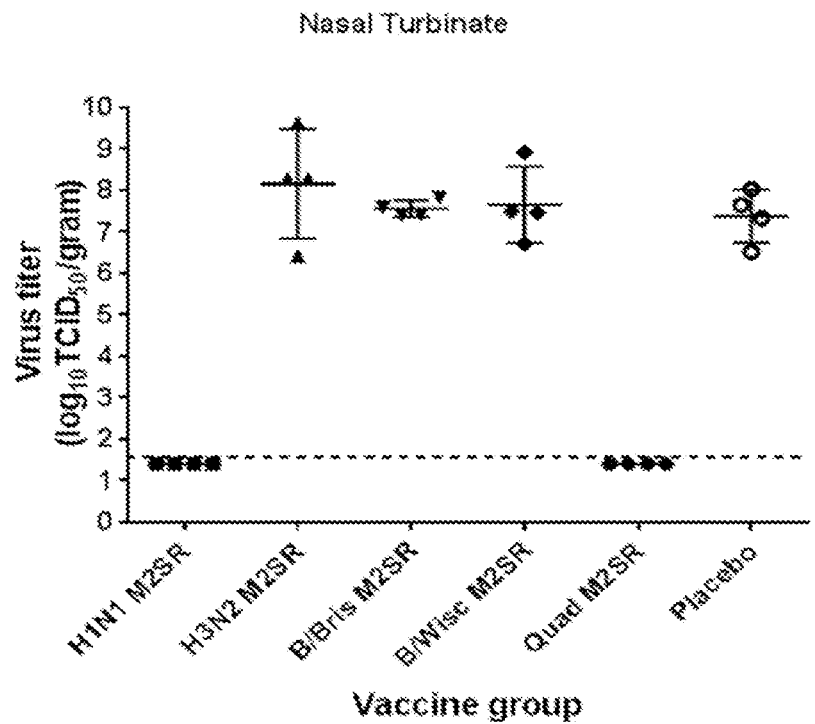
FIG. 13A is a chart showing virus titer in nasal turbinate tissue on day 3 post influenza A challenge.
Figure 13B:
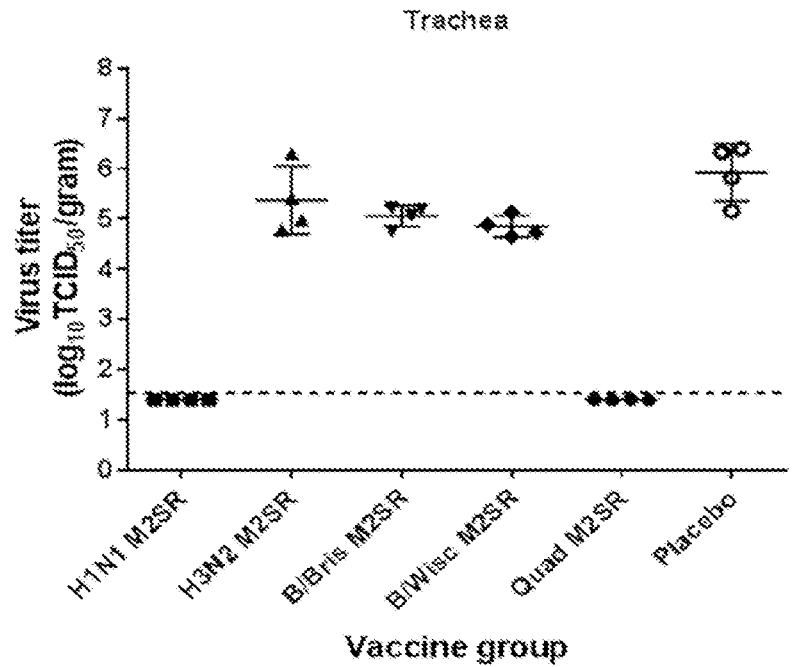
FIG. 13B is a chart showing virus titer in trachea tissue on day 3 post influenza A challenge.
Figure 13C:
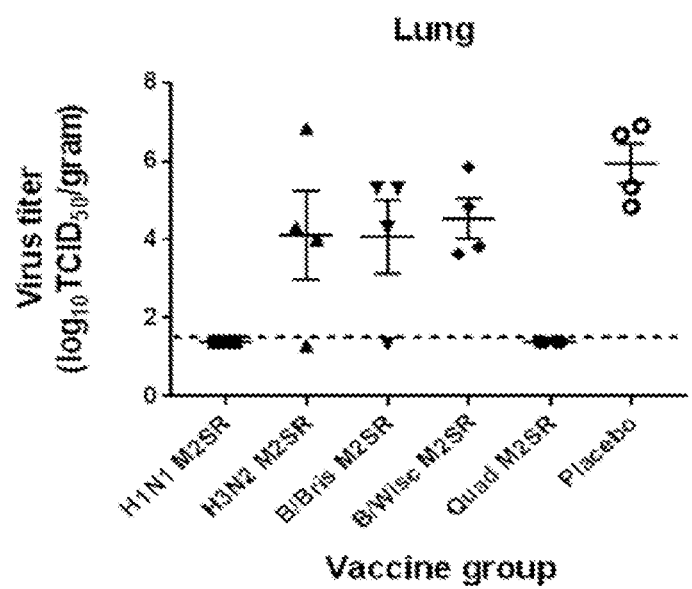
FIG. 13C is a chart showing virus titer in lung tissue on day 3 post influenza A challenge.

Example 8: Quadrivalent M2SR vaccine protects mice from lethal influenza A virus challenge BALB/c female mice (N=4) were challenged with a lethal dose of a heterologous influenza A virus, such as A/Aichi/02/1968 (H3N2) virus (40 mouse 50% lethal dose ($MLD_{50}$)), 22 days after inoculation. All mice vaccinated with the trivalent (comprising H1N1 (comprising an M2SR-1 mutant comprising SEQ ID NO: 1), H3N2 (comprising an M2SR-1 mutant comprising SEQ ID NO: 1), and B/Yamagata (comprising a BM2SR-4 mutant comprising SEQ ID NO: 9)) or quadrivalent M2SR vaccines (comprising H1N1 (comprising an M2SR-1 mutant comprising SEQ ID NO: 1), H3N2 (comprising an M2SR-1 mutant comprising SEQ ID NO: 1), B/Victoria lineage (comprising a BM2SR-4 mutant comprising SEQ ID NO: 9), and B/Yamagata (comprising a BM2SR-4 mutant comprising SEQ ID NO: 9)) had more survivors after challenge (FIG. 9B) and lost transient weight but started recovery on day 7 (FIG. 9A). The control mice given only PBS, however, lost body weight and did not survive 7 days past the challenge date. These results demonstrate that trivalent and quadrivalent M2SR/BM2SR vaccines confer cross-protection against the challenge virus that does not match any vaccine component.

Example 9: Immune Responses Elicited by Monovalent M2SR and BM2SR and Quadrivalent M2SR Vaccines and Protective Efficacy in the Ferret Model A. Summary This example demonstrates that the immune responses elicited by the Quadrivalent M2SR vaccine are similar to each of the monovalent M2SR and BM2SR vaccines in the ferret model. That is, the Quadrivalent M2SR does not display interference and elicits protective immune responses against each of the components. Each of the M2SR and BM2SR candidate viruses were administered intranasally to 12 male ferrets at a dose level of $1 \times 10^7$ $TCID_{50}$ (monovalents) or $4 \times 10^7$ $TCID_{50}$ (quadrivalent). As a control, one group of ferrets was administered OPTI-MEMTM as a placebo control. A prime-boost vaccination regimen was utilized for each treatment group. Ferrets were administered the prime vaccine (day 0) and the boost vaccination 28 days later (day 28). Following each vaccination, ferrets were observed for 14 days post inoculation for mortality, with body weights, body temperatures and clinical signs measured daily. Serum was collected on days 21, 35, and 56 from all ferrets post-vaccination to evaluate antibody levels over time.

All animals were challenged intranasally on Day 70 with $1 \times 10^6$ PFU of A/California/07/2009 (H1N1pdm). Following challenge, ferrets were monitored for 14 days post inoculation for mortality, with body weights, body temperatures, and clinical signs measured daily. Nasal washes were collected on days 1, 3, 5, and 7 post challenge from ferrets (N=8) in each group for viral titers. Additionally, serum was collected post-challenge (day 82) from surviving ferrets for analysis. Necropsy was performed on 4 ferrets per group 3 days (day 73) post challenge. Organs were collected for determination of viral load (titers) after challenge.

No vaccine-related adverse events were observed among the 5 groups. After challenge, the placebo control group exhibited a reduction (~15%) in weight. A reduction in weight was also observed in the antigenically mismatched monovalent H3N2 M2SR and BM2SR vaccinated groups; however, the reduction (~5-8%) was less than that observed in the placebo group. The Quadrivalent M2SR and H1N1pdm M2SR did not display any significant weight loss after challenge.

B. Materials and Methods

Vaccine Virus Inoculation. Ferrets were inoculated intranasally with either two doses of a monovalent M2SR or BM2SR vaccine at a dose of $1 \times 10^7$ $TCID_{50}$ or inoculated intranasally with two doses of a quadrivalent M2SR vaccine at a dose of $4 \times 10^7$ $TCID_{50}$ as shown in Table B. A vial of frozen stock was thawed at room temperature for at least 10 minutes and then stored refrigerated (or on wet ice) until use. Ferrets were anesthetized with ketamine/xylazine and the virus dose administered intranasally in a volume of 500 μL (250 μL per nare). Animals were observed daily for 7 days after each vaccination. Body weights, body temperatures, and clinical signs were monitored for 7 days.

TABLE B

Vaccination and sample collection schedule

| Group | Vaccine Virus | N | Dose (TCID$_{50}$)[1] | Vaccination (days) | Challenge (day) | Nasal Washes[2] (days) | Organs[3] n = 3 (day) | Serum collections[4] |
|---|---|---|---|---|---|---|---|---|
| 1 | Vehicle (Control) | 12 | N/A | 0, 28 | 70 | 71, 73, 75, 77 | 73 | 21, 35, 56, 82 |
| 2 | H1N1 M2SR | 12 | $10^7$ | 0, 28 | 70 | 71, 73, 75, 77 | 73 | 21, 35, 56, 82 |
| 3 | H3N2 M2SR | 12 | $10^7$ | 0, 28 | 70 | 71, 73, 75, 77 | 73 | 21, 35, 56, 82 |
| 4 | B/Bris BM2SR | 12 | $10^7$ | 0, 28 | 70 | 71, 73, 75, 77 | 73 | 21, 35, 56, 82 |
| 5 | B/Wisc BM2SR | 12 | $10^7$ | 0, 28 | 70 | 71, 73, 75, 77 | 73 | 21, 35, 56, 82 |
| 6 | Quad M2SR | 12 | $4 \times 10^7$ | 0, 28 | 70 | 71, 73, 75, 77 | 73 | 21, 35, 56, 82 |

[1]Inoculated intranasally
[2]Nasal Washes collected from animals not assigned for necropsy.
[3]Organs (nasal turbinate, trachea, lung (left and right cranial and caudal lobes) collected from 4 ferrets per group for viral titer analysis.
[4]Post vaccination serum collections The M2SR virus is a recombinant influenza A virus that does not express a functional M2 protein, comprising an M2SR-1 mutant comprising SEQ ID NO: 1, encoding the HA and NA genes of Influenza A/Brisbane/10/2007-like A/Uruguay/716/2007(H3N2) or A/California/07/2009 (H1N1pdm). The BM2SR virus is a recombinant influenza B virus that does not express a functional BM2 protein, comprising a BM2SR-0 mutant comprising SEQ ID NO: 11, encoding the HA and NA of B/Brisbane/60/2008 (Victoria) or B/Wisconsin/01/2010 (Yamagata). The Quadrivalent M2SR is composed of 2 M2SR and 2 BM2SR viruses that encode for H1N1, H3N2, B/Victoria, B/Yamagata HA and NA.

Animals and Animal Care. Eighty male ferrets were purchased from Triple F Farms and 72 of the ferrets were placed on study. Animals were approximately 4 months of age at the time of study initiation. The animals were certified by the supplier to be healthy and free of antibodies to infectious diseases. Upon arrival the animals were single housed in suspended wire cages with slat bottoms, suspended over paper-lined waste pans. The animal room and cages had been cleaned and sanitized prior to animal receipt, in accordance with accepted animal care practices and relevant standard operating procedures. Certified Teklad Global Ferret Diet #2072 (Teklad Diets, Madison WI) and city of Chicago tap water were provided ad libitum and were refreshed at least three time per week. Fluorescent lighting in the animal rooms was maintained on a 12-hr light/dark cycle. Animal room temperature and relative humidity were within respective protocol limits and ranged from 20.0 to 25.0° C. and 30 to 63%, respectively, during the study.

Animal Quarantine and Randomization. The ferrets were held in quarantine for seven days prior to randomization and observed daily. Based on daily observations indicating general good health of the animals, the ferrets were released from quarantine for randomization and testing. Following quarantine, ferrets were weighed and assigned to treatment groups using a computerized randomization procedure based on body weights that produced similar group mean values [ToxData® version 2.1.E.11 (PDS Pathology Data Systems, Inc., Basel, Switzerland)]. Within a group, all body weights were within 20% of their mean. Animals selected for the study receive a permanent identification number by ear tag and transponder and individual cage cards also identified the study animals by individual numbers and group. The identifying numbers assigned were unique within the study.

Experimental Design. To assess the vaccine efficacy, ferrets were immunized with each M2SR, BM2SR, or Quadrivalent M2SR virus or mock immunized by medium (OPTI-MEM™). Ferret body weight, body temperature, and clinical symptoms were monitored and immunological responses evaluated. 72 male ferrets (Triple F Farms, Sayre PA), 4 months of age at the time of study initiation, were utilized for the study. All animal procedures were performed in an animal biosafety level-2 facility in accordance with the protocols approved by the animal care and use committee at IIT Research Institute. Prior to inoculation, ferrets were monitored for 3 days to measure body weight and establish baseline body temperatures. Temperature readings were recorded daily through a transponder (BioMedic data systems, Seaford, DE) implanted subcutaneously in each ferret. Blood was collected prior to study initiation, and serum tested for influenza antibodies. Pre-vaccination serum samples were treated with receptor destroying enzyme (RDE) to remove nonspecific inhibitors, then serially diluted, tested against a defined amount of influenza virus A/California/07/2009-like (H1N1pdm), A/Switzerland/9715293/2013 (H3N2), Influenza B Virus, B/Brisbane/60/2008 (Victoria Lineage) and B/Wisconsin/01/2010 (Yamagata Lineage) and mixed with 0.5% turkey red blood cells or 0.75-1.0% guinea pig red blood cells. Antibody titers are defined by the lowest serum dilution causing inhibition of red blood cell agglutination. Only ferrets with HAI (hemagglutination inhibition) titers less than 40 were considered seronegative and used in this study. Study animals were randomized and divided into 6 groups (12 ferrets/group) as shown in Table B.

Ferrets were inoculated intranasally with a single dose of 1×10$^7$ TCID$_{50}$ of M2SR or BM2SR virus on days 0 and 28, or a single dose of 4×10$^7$ TCID$_{50}$ of Quadrivalent M2SR on days 0 and 28. Control group was mock inoculated intranasally with OPTI-MEMTM on days 0 and 28. Ferret body temperatures, weights, and clinical symptoms were monitored daily for 14 days post-inoculations. Nasal wash samples were kept at −65° C. Blood was collected prior to inoculation (day −3 to −5) and days 21, 35 and 56 and serum kept at −65° C. until measurement of antibody titer by ELISA and HAI assay.

C. Results

Anti-HA IgG antibody titers from the serum samples were determined by enzyme-linked immunosorbent assay (ELISA) against A/Brisbane/10/2007 (H3N2), A/California/07/2009 (H1N1pdm), B/Wisconsin/01/2010 (Yamagata lineage), and B/Brisbane/60/2008 (Victoria lineage). Briefly, ELISA plates were coated by recombinant HA protein from each strain, blocked by bovine serum albumin (BSA), and samples were applied. Ferret IgG antibodies were detected by horseradish peroxidase labeled anti-ferret IgG- goat antibodies (KPL, Inc., Gaithersburg, MD) and SureBlue TMB (KPL, Inc.) substrate.

As expected, ferrets in each of the immunized groups showed significant elevation of anti-HA antibody in serum to its respective antigen. More importantly, the Quadrivalent M2SR groups demonstrated significant elevation of anti-HA antibody in serum against all four antigens (FIG. 10) indicating that there is no interference between the components of the multivalent formulation. These data suggest that the M2SR, BM2SR, and Quadrivalent M2SR viruses elicit significant immune responses in ferrets.

Serum samples were analyzed by Hemagglutination Inhibition (HAI) assay to demonstrate functional activity of the antibodies detected by ELISA. Serum samples were treated with receptor-destroying enzyme (RDE) (Denka Seiken, Tokyo, Japan) to eliminate inhibitors of nonspecific hemagglutination. RDE was reconstituted per the manufacturer's instructions. Serum was diluted 1:3 in RDE and incubated 18-20 hours in a 37° C.±2° C. water bath. After the addition of an equal volume of 2.5% (v/v) sodium citrate, the samples were incubated in a 56±2° C. water bath for 30±5 minutes. 0.85% NaCl was added to each sample to a final serum dilution of 1:10 after the RDE treatment. The diluted samples were then diluted into four two-fold dilutions (1:10 to 1:80) in duplicate in phosphate buffered saline (PBS) then incubated with 4 hemagglutinating units of A/Brisbane/10/2007 (H3N2), A/California/07/2009 (H1N1pdm), B/Wisconsin/01/2010 (Yamagata lineage) and B/Brisbane/60/2008 (Victoria lineage) influenza viruses. After incubation, 0.5% avian red blood cells were added to each sample and incubated for 30±5 minutes. Presence or absence of hemagglutination was then scored.

As shown in FIGS. 11A and 11B, all M2SR immunized ferrets demonstrated significant HAI antibody titers against their respective test virus. The Quadrivalent M2SR demonstrated significant HAI titers against all four test viruses. The placebo (naïve) group did not elicit any influenza specific antibodies. The CDC states that serum HAI antibody titers of 40 are associated with at least a 50% reduction in risk for influenza infection or disease in populations. Therefore, these results suggest that M2SR and BM2SR viruses elicit protective immune responses that are maintained when the viruses are formulated together as a Quadrivalent vaccine.

After challenge with A/California/09/2009 (H1N1pdm), a 5-8% loss of body weight was observed by Day 6 post challenge in all animals. Throughout the 14-day observation period, animal body weights remained below their initial weight, except the OPTI-MEM™-administered ferrets (placebo group) lost the most weight (15%). Weight loss among vaccinated ferrets was dependent on the antigenicity of the vaccine. Ferrets receiving the matching H1N1pdm M2SR or the Quadrivalent M2SR (that contains the H1N1pdm M2SR) did not display any significant weight loss. Ferrets receiving a heterologous H3N2 M2SR or either of the BM2SR vaccines displayed ~5-8% weight loss.

Nasal wash samples were collected from all ferrets on days 1, 3, 5, 7 post-challenge and evaluated for the presence of challenge virus by plaque assay in MDCK cells. FIG. 12 shows that the Quadrivalent M2SR controlled challenge virus replication in a manner similar to the monovalent homologous H1N1pdm M2SR. The placebo and BM2SR monovalent vaccines did not control the challenge virus with at least 5 logs of virus being detected up to 5 days post-infection. The heterologous H3N2 M2SR group did not eliminate the challenge virus like the homologous H1N1 and Quad M2SR but did partially control virus replication relative to the placebo group.

Respiratory organs harvested on day 3 post-infection from 4 ferrets demonstrated the control of challenge virus. The H1N1 M2SR and Quad M2SR did not allow the challenge virus to replicate in the upper and lower respiratory tissues at all (nasal turbinate, trachea, lung) as shown in FIGS. 13A, 13B, and 13C). In contrast, the challenge virus grew to high titers in the upper respiratory tissues (nasal turbinate and trachea) of the other groups. In the lower respiratory tract (lung), the monovalent M2SR vaccines controlled the challenge virus relative to the placebo group. These results suggest that the homologous and Quadrivalent M2SR prevent influenza infection from establishing itself and that the unrelated M2SR vaccines reduce severity of infection.

D. Conclusion

This example shows that intranasal administration of the Quadrivalent M2SR vaccine virus was not associated with any vaccine-related adverse events (e.g., elevated body temperature, loss of weight, or clinical signs). These results show that the Quadrivalent M2SR virus elicits protective immune responses against each strain contained in the multivalent formulation and is useful as an intranasal influenza vaccine.

5What is claimed is:

1. An immunogenic composition, wherein the composition is a quadrivalent composition consisting of:

a) two engineered attenuated influenza A viruses consisting of:

i) H1N1 having a mutant M2 gene comprising SEQ ID NO: 1, and ii) H3N2 having a mutant M2 gene comprising SEQ ID NO: 1; and b) two engineered attenuated influenza B viruses consisting of:

i) B/Victoria having a mutant BM2 gene comprising SEQ ID NO: 9, and ii) B/Yamagata having a mutant BM2 gene comprising SEQ ID NO: 9.

2. The immunogenic composition of claim 1, wherein the composition is formulated for intranasal or intracutaneous administration.

3. A method of stimulating an immune response against influenza A and influenza B comprising administering to a subject in need thereof a quadrivalent immunogenic composition consisting of a) two engineered attenuated influenza A viruses consisting of:

i) H1N1 having a mutant M2 gene comprising SEQ ID NO: 1, and ii) H3N2 having a mutant M2 gene comprising SEQ ID NO: 1; and b) two engineered attenuated influenza B viruses consisting of:

i) B/Victoria having a mutant BM2 gene comprising SEQ ID NO: 9, and ii) B/Yamagata having a mutant BM2 gene comprising SEQ ID NO: 9.

4. The method of claim 3, wherein the immunogenic composition is formulated for intranasal or intracutaneous administration.

5. An immunogenic composition, wherein the composition is a quadrivalent composition consisting of a) two engineered attenuated influenza A viruses consisting of:

i) H1N1 having a mutant M2 gene comprising SEQ ID NO: 1, and ii) H3N2 having a mutant M2 gene comprising SEQ ID NO: 1; and b) two engineered attenuated influenza B viruses consisting of:

i) B/Victoria having a mutant BM2 gene comprising SEQ ID NO: 11, and ii) B/Yamagata having a mutant BM2 gene comprising SEQ ID NO: 11.

6. The immunogenic composition of claim 5, wherein the composition is formulated for intranasal or intracutaneous administration.

7. A method of stimulating an immune response against influenza A and influenza B comprising administering to a subject in need thereof a quadrivalent immunogenic composition consisting of a) two engineered attenuated influenza A viruses consisting of:

i) H1N1 having a mutant M2 gene comprising SEQ ID NO: 1, and ii) H3N2 having a mutant M2 gene comprising SEQ ID NO: 1; and b) two engineered attenuated influenza B viruses consisting of:

i) B/Victoria having a mutant BM2 gene comprising SEQ ID NO: 11, and ii) B/Yamagata having a mutant BM2 gene comprising SEQ ID NO: 11.

8. The method of claim 7, wherein the immunogenic composition is formulated for intranasal or intracutaneous administration.

* * * * *

SEQUENCE LISTING

```
<160> NUMBER OF SEQ ID NOS: 14

<210> SEQ ID NO 1
<211> LENGTH: 976
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
agcaaaagca ggtagatatt gaaagatgag tcttctaacc gaggtcgaaa cgtacgtact     60
ctctatcatc ccgtcaggcc ccctcaaagc cgagatcgca cagagacttg aagatgtctt    120
```

```
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgattaata ggatcgtctt tttttcaaat gcatttaccg tcgctttaaa tacgactga    840 aaggagggcc ttctacggaa ggagtgccaa agtctatgag ggaagaatat cgaaaggaac    900
agcagagtgc tgtggatgct gacgatggtc attttgtcag catagagctg gagtaaaaaa    960
ctaccttgtt tctact                                                   976
```

<210> SEQ ID NO 2
<211> LENGTH: 1027
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 2

```
agcaaaagca ggtagatatt gaaagatgag tcttctaacc gaggtcgaaa cctacgtact     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgattaata gactattgcc gcaaatatca ttgggatctt gcacttgaca ttgtggattc    840
ttgatcgtct tttttcaaa tgcatttacc gtcgctttaa atacgactg aaaggagggc    900 cttctacgga aggagtgcca agtctatga gggaagaata tcgaaaggaa cagcagagtg    960
ctgtggatgc tgacgatggt cattttgtca gcatagagct ggagtaaaaa actaccttgt   1020
ttctact                                                            1027
```

```
<210> SEQ ID NO 3
<211> LENGTH: 976
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
agcaaaagca ggtagatatt gaaagatgag tcttctaacc gaggtcgaaa cctacgtact       60
ctctatcatc ccgtcaggcc ccctcaaagc cgagatcgca cagagacttg aagatgtctt     120
tgcagggaag aacaccgatc ttgaggttct catggaatgg ctaaagacaa gaccaatcct     180
gtcacctctg actaagggga ttttaggatt tgtgttcacg ctcaccgtgc ccagtgagcg     240
aggactgcag cgtagacgct ttgtccaaaa tgcccttaat gggacgggga tccaaataa      300 catggacaaa gcagttaaac tgtataggaa gctcaagagg gagataacat ccatggggc      360 caaagaaatc tcactcagtt attctgctgg tgcacttgcc agttgtatgg gcctcatata     420
caacaggatg ggggctgtga ccactgaagt ggcatttggc ctggtatgtg caacctgtga     480
acagattgct gactcccagc atcggtctca taggcaaatg gtgacaacaa ccaatccact     540
aatcagacat gagaacagaa tggttttagc cagcactaca gctaaggcta tggagcaaat     600
ggctggatcg agtgagcaag cagcagaggc catggaggtt gctagtcagg ctagacaaat     660
ggtgcaagcg atgagaacca tgggactca tcctagctcc agtgctggtc tgaaaaatga     720
tcttcttgaa aatttgcagg cctatcagaa acgaatgggg gtgcagatgc aacggttcaa     780
gtgattaata ggatcgtctt tttttcaaat gcatttaccg tcgctttaaa tacgactga     840 aaggagggcc ttctacggaa ggagtgccaa agtctatgag gaagaatat cgaaaggaac      900 agcagagtgc tgtggatgct gacgatggtc attttgtcag catagagctg gagtaaaaaa     960
ctaccttgtt tctact                                                     976

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Ser Leu Leu Thr Glu Val Glu Thr Pro Ile Arg Asn Glu Trp Gly
1               5                   10                  15

Cys Arg Cys Asn Gly Ser Ser Asp
            20

<210> SEQ ID NO 5
<211> LENGTH: 1027
<212> TYPE: DNA
<213> ORGANISM: Influenza A virus

<400> SEQUENCE: 5
agcaaaagca ggtagatatt gaaagatgag tcttctaacc gaggtcgaaa cgtacgtact       60
ctctatcatc ccgtcaggcc ccctcaaagc cgagatcgca cagagacttg aagatgtctt     120
tgcagggaag aacaccgatc ttgaggttct catggaatgg ctaaagacaa gaccaatcct     180
gtcacctctg actaagggga ttttaggatt tgtgttcacg ctcaccgtgc ccagtgagcg     240
aggactgcag cgtagacgct ttgtccaaaa tgcccttaat gggacgggga tccaaataa      300
```

| | |
|---|---|
| catggacaaa gcagttaaac tgtataggaa gctcaagagg gagataacat tccatggggc | 360 |
| caaagaaatc tcactcagtt attctgctgg tgcacttgcc agttgtatgg gcctcatata | 420 |
| caacaggatg ggggctgtga ccactgaagt ggcatttggc ctggtatgtg caacctgtga | 480 |
| acagattgct gactcccagc atcggtctca taggcaaatg gtgacaacaa ccaatccact | 540 |
| aatcagacat gagaacagaa tggttttagc cagcactaca gctaaggcta tggagcaaat | 600 |
| ggctggatcg agtgagcaag cagcagaggc catggaggtt gctagtcagg ctagacaaat | 660 |
| ggtgcaagcg atgagaacca ttgggactca tcctagctcc agtgctggtc tgaaaaatga | 720 |
| tcttcttgaa aatttgcagg cctatcagaa acgaatgggg gtgcagatgc aacggttcaa | 780 |
| gtgatcctct cactattgcc gcaaatatca ttgggatctt gcacttgaca ttgtggattc | 840 |
| ttgatcgtct ttttttcaaa tgcatttacc gtcgctttaa atacgactg aaaggagggc | 900 |
| cttctacgga aggagtgcca agtctatga gggaagaata tcgaaggaa cagcagagtg | 960 |
| ctgtggatgc tgacgatggt cattttgtca gcatagagct ggagtaaaaa actaccttgt | 1020 |
| ttctact | 1027 |

<210> SEQ ID NO 6
<211> LENGTH: 861
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

| | |
|---|---|
| agcagaagca cgcactttct taaaatgtcg ctgtttggag acacaattgc ctacctgctt | 60 |
| tcattgacag aagatggaga aggcaaagca gaactagcag aaaaattaca ctgttggttc | 120 |
| ggtgggaaag aatttgacct agactctgcc ttggaatgga taaaaaacaa agatgctta | 180 |
| actgacatac agaaagcact aattggcgcc tctatctgct ttttaaaacc caaagaccag | 240 |
| gaaagaaaaa gaagattcat cacagagccc tatcaggaa tggggacaac agcaacaaaa | 300 |
| aagaagggcc tgattctagc tgagagaaaa atgagaagat gtgtgagctt ccatgaagca | 360 |
| tttgaaatag cagaaggcca tgaaagctca gcgttactat attgtctcat ggtcatgtac | 420 |
| ctgaatcctg gaaattattc aatgcaagta aaactaggaa cgctctgtgc tttgtgcgaa | 480 |
| aaacaagcat cacattcaca cagggctcat agcagagcag cgagatcttc agtgcctgga | 540 |
| gtgagacggg aaatgcagat ggtctcagct atgaacacag caaaaacaat gaatggaatg | 600 |
| ggaaaaggag aagacgttca aaaactggca gaagaactgc aaagcaacat ggagtattg | 660 |
| agatcttctg gggcaagtca aagaatggg gaaggaattg caaggatgt aatggaagtg | 720 |
| ctaaagcaga gctctatggg aaattcagct cttgtgaaga ataccctata aattcaattt | 780 |
| ttactgtact tcttactatg catttaagca aattgtaatc aatgtcagca ataaactgg | 840 |
| aaaaagtgcg ttgtttctac t | 861 |

<210> SEQ ID NO 7
<211> LENGTH: 904
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

| | |
|---|---|
| agcagaagca cgcactttct taaaatgtcg ctgtttggag acacaattgc ctacctgctt | 60 |

```
tcattgacag aagatggaga aggcaaagca gaactagcag aaaaattaca ctgttggttc      120
ggtgggaaag aatttgacct agactctgcc ttggaatgga taaaaaacaa aagatgctta      180
actgacatac agaaagcact aattggcgcc tctatctgct tttttaaaacc caaagaccag     240 gaaagaaaaa gaagattcat cacagagccc ctatcaggaa tggggacaac agcaacaaaa     300
aagaagggcc tgattctagc tgagagaaaa atgagaagat gtgtgagctt ccatgaagca     360
tttgaaatag cagaaggcca tgaaagctca gcgttactat attgtctcat ggtcatgtac     420
ctgaatcctg gaaattattc aatgcaagta aaactaggaa cgctctgtgc tttgtgcgaa     480
aaacaagcat cacattcaca cagggctcat agcagagcag cgagatcttc agtgcctgga     540
gtgagacggg aaatgcagat ggtctcagct atgaacacag caaaaacaat gaatggaatg     600
ggaaaaggag aagacgttca aaaactggca gaagaactgc aaagcaacat tggagtattg     660
agatctcttg gggcaagtca aaagaatggg gaaggaattg caaggatgt aatggaagtg      720 ctaaagcaga gctctatggg aaattcagct cttgtgaaga aatacctata atgctcgaac     780
catttcagat tctttcaatt tgttagatag ctaaattcaa tttttactgt acttcttact     840
atgcatttaa gcaaattgta atcaatgtca gcaaataaac tggaaaaagt gcgttgtttc     900
tact                                                                  904

<210> SEQ ID NO 8
<211> LENGTH: 904
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
agcagaagca cgcactttct taaaatgtcg ctgtttggag acacaattgc ctacctgctt       60
tcattgacag aagatggaga aggcaaagca gaactagcag aaaaattaca ctgttggttc      120
ggtgggaaag aatttgacct agactctgcc ttggaatgga taaaaaacaa aagatgctta      180
actgacatac agaaagcact aattggcgcc tctatctgct tttttaaaacc caaagaccag     240 gaaagaaaaa gaagattcat cacagagccc ctatcaggag tggggacaac agcaacaaaa     300
aagaagggcc tgattctagc tgagagaaaa atgagaagat gtgtgagctt ccatgaagca     360
tttgaaatag cagaaggcca tgaaagctca gcgttactat attgtctcat ggtcatgtac     420
ctgaatcctg gaaattattc aatgcaagta aaactaggaa cgctctgtgc tttgtgcgaa     480
aaacaagcat cacattcaca cagggctcat agcagagcag cgagatcttc agtgcctgga     540
gtgagacggg aaatgcagat ggtctcagct atgaacacag caaaaacaat gaatggaatg     600
ggaaaaggag aagacgttca aaaactggca gaagaactgc aaagcaacat tggagtattg     660
agatctcttg gggcaagtca aaagaatggg gaaggaattg caaggatgt aatggaagtg      720 ctaaagcaga gctctatggg aaattcagct cttgtgaaga aatacctata atgctcgaac     780
catttcagat tctttcaatt tgttagatag ctaaattcaa tttttactgt acttcttact     840
atgcatttaa gcaaattgta atcaatgtca gcaaataaac tggaaaaagt gcgttgtttc     900
tact                                                                  904

<210> SEQ ID NO 9
<211> LENGTH: 1111
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 9

```
agcagaagca cgcactttct taaaatgtcg ctgtttggag acacaattgc ctacctgctt    60
tcattgacag aagatggaga aggcaaagca gaactagcag aaaaattaca ctgttggttc   120
ggtgggaaag aatttgacct agactctgcc ttggaatgga taaaaaacaa aagatgctta   180
actgacatac agaaagcact aattggcgcc tctatctgct ttttaaaacc caaagaccag   240
gaaagaaaaa gaagattcat cacagagccc tatcaggaa tggggacaac agcaacaaaa   300
aagaagggcc tgattctagc tgagagaaaa atgagaagat gtgtgagctt ccatgaagca   360
tttgaaatag cagaaggcca tgaaagctca gcgttactat attgtctcat ggtcatgtac   420
ctgaatcctg gaaattattc aatgcaagta aaactaggaa cgctctgtgc tttgtgcgaa   480
aaacaagcat cacattcaca cagggctcat agcagagcag cgagatcttc agtgcctgga   540
gtgagacggg aaatgcagat ggtctcagct atgaacacag caaaaacaat gaatggaatg   600
ggaaaaggag aagacgttca aaaactggca gaagaactgc aaagcaacat tggagtattg   660
agatctcttg gggcaagtca aaagaatggg gaaggaattg caaggatgt aatggaagtg   720 ctaaagcaga gctctatggg aaattcagct cttgtgaaga atacctata atgctcgaac   780 catttcagat tctttcaatt tgttagatag ctaaaagggg ccaaataaag agacaataaa   840
cagagaggta tcaattttga gacacagtta ccaaaaagaa atccaggcca agaagcaat   900 gaaggaagta ctctctgaca acatggaggt attgagtgac cacatagtaa ttgaggggct   960
ttctgctgaa gagataataa aaatgggtga acagttttg gaggtagaag aattgcatta  1020
aattcaattt ttactgtact tcttactatg catttaagca aattgtaatc aatgtcagca  1080
aataaactgg aaaaagtgcg ttgtttctac t                                 1111
```

<210> SEQ ID NO 10
<211> LENGTH: 1111
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10

```
agcagaagca cgcactttct taaaatgtcg ctgtttggag acacaattgc ctacctgctt    60
tcattgacag aagatggaga aggcaaagca gaactagcag aaaaattaca ctgttggttc   120
ggtgggaaag aatttgacct agactctgcc ttggaatgga taaaaaacaa aagatgctta   180
actgacatac agaaagcact aattggcgcc tctatctgct ttttaaaacc caaagaccag   240
gaaagaaaaa gaagattcat cacagagccc tatcaggag tggggacaac agcaacaaaa   300
aagaagggcc tgattctagc tgagagaaaa atgagaagat gtgtgagctt ccatgaagca   360
tttgaaatag cagaaggcca tgaaagctca gcgttactat attgtctcat ggtcatgtac   420
ctgaatcctg gaaattattc aatgcaagta aaactaggaa cgctctgtgc tttgtgcgaa   480
aaacaagcat cacattcaca cagggctcat agcagagcag cgagatcttc agtgcctgga   540
gtgagacggg aaatgcagat ggtctcagct atgaacacag caaaaacaat gaatggaatg   600
ggaaaaggag aagacgttca aaaactggca gaagaactgc aaagcaacat tggagtattg   660
agatctcttg gggcaagtca aaagaatggg gaaggaattg caaggatgt aatggaagtg   720
```

-continued

```
ctaaagcaga gctctatggg aaattcagct cttgtgaaga aatacctata atgctcgaac    780
catttcagat tctttcaatt tgttagatag ctaaaagggg ccaaataaag agacaataaa    840
cagagaggta tcaattttga gacacagtta ccaaaaagaa atccaggcca aagaagcaat    900
gaaggaagta ctctctgaca acatggaggt attgagtgac cacatagtaa ttgaggggct    960
ttctgctgaa gagataataa aaatgggtga aacagttttg gaggtagaag aattgcatta   1020
aattcaattt ttactgtact tcttactatg catttaagca aattgtaatc aatgtcagca   1080
aataaactgg aaaaagtgcg ttgtttctac t                                  1111

<210> SEQ ID NO 11
<211> LENGTH: 862
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 11
agcagaagca cgcactttct taaaatgtcg ctgtttggag acacaattgc ctacctgctt     60
tcactaatag aagatggaga aggcaaagca gaactagctg aaaaattaca ctgttggttc    120
ggtgggaaag aatttgacct agattctgct ttggaatgga taaaaaacaa aaggtgccta    180
actgatatac aaaaagcact aattggtgcc tctatatgct ttttaaaacc caaagaccaa    240
gaaagaaaaa ggagattcat cacagagccc ctgtcaggaa tgggaacaac agcaacaaag    300
aagaaaggcc taattctagc tgagagaaaa atgagaagat gtgtaagctt tcatgaagca    360
tttgaaatag cagaaggcca cgaaagctca gcattactat attgtcttat ggtcatgtac    420
ctaaaccctg aaaactattc aatgcaagta aaactaggaa cgctctgtgc tttatgcgag    480
aaacaagcat cgcactcgca tagagcccat agcagagcag caaggtcttc ggtacctgga    540
gtaagacgag aaatgcagat ggtttcagct atgaacacag caaagacaat gaatggaatg    600
ggaaagggag aagacgtcca aaaactagca gaagagctgc aaaacaacat tggagtgttg    660
agatctctag gagcaagtca aaagaatgga gaaggaattg ccaaagatgt aatggaagtg    720
ctaaaacaga gctctatggg aaattcagct cttgtgagga aatacttata agcccaattt    780
tcactgtatt tcttactatg catttaagca aattgtaatc aatgtcagtg aataaaactg    840
gaaaaagtgc gttgtttcta ct                                             862

<210> SEQ ID NO 12
<211> LENGTH: 1191
<212> TYPE: DNA
<213> ORGANISM: Influenza B virus
<400> SEQUENCE: 12
agcagaagca cgcactttct taaaatgtcg ctgtttggag acacaattgc ctacctgctt     60
tcactaatag aagatggaga aggcaaagca gaactagctg aaaaattaca ctgttggttc    120
ggtgggaaag aatttgacct agattctgct ttggaatgga taaaaaacaa aaggtgccta    180
actgatatac aaaaagcact aattggtgcc tctatatgct ttttaaaacc caaagaccaa    240
gaaagaaaaa ggagattcat cacagagccc ctgtcaggaa tgggaacaac agcaacaaag    300
aagaaaggcc taattctagc tgagagaaaa atgagaagat gtgtaagctt tcatgaagca    360
tttgaaatag cagaaggcca cgaaagctca gcattactat attgtcttat ggtcatgtac    420
ctaaaccctg aaaactattc aatgcaagta aaactaggaa cgctctgtgc tttatgcgag    480
```

```
aaacaagcat cgcactcgca tagagcccat agcagagcag caaggtcttc ggtacctgga      540
gtaagacgag aaatgcagat ggtttcagct atgaacacag caaagacaat gaatggaatg      600
ggaaagggag aagacgtcca aaaactagca gaagagctgc aaaacaacat tggagtgttg      660
agatctctag gagcaagtca aaagaatgga aaggaattg ccaaagatgt aatggaagtg       720
ctaaaacaga gctctatggg aaattcagct cttgtgagga atacttata atgctcgaac       780 cacttcagat tctttcaatt tgttctttca ttttatcagc tctccatttc atggcttgga      840
caatagggca tttgaatcaa ataagaagag gggtaaacct gaaaatacaa ataaggaatc      900
caaataagga ggcaataaac agagaggtgt caattctgag acacaattac caaaaggaaa      960
tccaagccaa agaacaatg aagaaaatac tctctgacaa catggaagta ttgggtgacc       1020
acatagtagt tgaagggctt tcaactgatg agataataaa aatgggtgaa acagttttgg      1080
aggtggaaga attgcaatga gcccaatttt cactgtattt cttactatgc atttaagcaa      1140
attgtaatca atgtcagtga ataaaactgg aaaaagtgcg ttgtttctac t               1191

<210> SEQ ID NO 13
<211> LENGTH: 294
<212> TYPE: DNA
<213> ORGANISM: Influenza A virus

<400> SEQUENCE: 13
atgagtcttc taaccgaggt cgaaacgcct atcagaaacg aatgggggtg cagatgcaac       60
ggttcaagtg atcctctcac tattgccgca aatatcattg ggatcttgca cttgacattg       120
tggattcttg atcgtctttt tttcaaatgc atttaccgtc gctttaaata cggactgaaa       180
ggagggcctt ctacggaagg agtgccaaag tctatgaggg aagaatatcg aaaggaacag      240
cagagtgctg tggatgctga cgatggtcat tttgtcagca tagagctgga gtaa            294

<210> SEQ ID NO 14
<211> LENGTH: 421
<212> TYPE: DNA
<213> ORGANISM: Influenza B virus

<400> SEQUENCE: 14
atgctcgaac cacttcagat tctttcaatt tgttctttca ttttatcagc tctccatttc       60
atggcttgga caatagggca tttgaatcaa ataagaagag gggtaaacct gaaaatacaa      120
ataaggaatc caaataagga ggcaataaac agagaggtgt caattctgag acacaattac      180
caaaaggaaa tccaagccaa agaacaatg aagaaaatac tctctgacaa catggaagta       240
ttgggtgacc acatagtagt tgaagggctt tcaactgatg agataataaa aatgggtgaa      300
acagttttgg aggtggaaga attgcaatga gcccaatttt cactgtattt cttactatgc      360
atttaagcaa attgtaatca atgtcagtga ataaaactgg aaaaagtgcg ttgtttctac      420
t                                                                    421
```